(12) United States Patent
Drews

(10) Patent No.: US 10,865,442 B2
(45) Date of Patent: Dec. 15, 2020

(54) COMMON LINE SELECTOR VALVE FOR A SYSTEM

(71) Applicant: Illumina, Inc., San Diego, CA (US)

(72) Inventor: Bradley Kent Drews, Poway, CA (US)

(73) Assignee: ILLUMINA, INC., San Diego, CA (US)

( * ) Notice: Subject to any disclaimer, the term of this patent is extended or adjusted under 35 U.S.C. 154(b) by 304 days.

(21) Appl. No.: 15/841,095

(22) Filed: Dec. 13, 2017

(65) Prior Publication Data

US 2018/0187255 A1 Jul. 5, 2018

Related U.S. Application Data

(60) Provisional application No. 62/442,677, filed on Jan. 5, 2017.

(30) Foreign Application Priority Data

Mar. 24, 2017 (GB) .................................. 1704761.4

(51) Int. Cl.
*C12Q 1/6869* (2018.01)
*B01L 3/00* (2006.01)

(52) U.S. Cl.
CPC ........ *C12Q 1/6869* (2013.01); *B01L 3/50273* (2013.01); *B01L 3/502738* (2013.01);
(Continued)

(58) Field of Classification Search
CPC ............. C12Q 1/6869; B01L 3/502738; B01L 3/50273; B01L 2300/0883; B01L 2400/0644; B01L 2300/0819; B01L 2400/0622; B01L 2200/027; B01L 3/502715; B01L 2300/0877; B01L 2400/0478; B01L 2200/16; B01L 2200/143; B01L 3/502769; B01L 2300/0864; B01L 3/022; B01L 3/0224; B01L 2300/0636; B01L 2400/0409; B01L 2200/0663;
(Continued)

(56) References Cited

U.S. PATENT DOCUMENTS

| 8,313,643 | B1 | 11/2012 | Baltimore |
| 8,354,080 | B2* | 1/2013 | Tsao .................. B01L 3/502723 |
| | | | 422/554 |
| 10,087,440 | B2* | 10/2018 | Lofquist ........... B01L 3/502753 |
| 10,625,260 | B2* | 4/2020 | Drews ................. B01L 3/50273 |

(Continued)

FOREIGN PATENT DOCUMENTS

| WO | 98/03264 | 1/1998 |
| WO | 00/37163 | 6/2000 |
| WO | 2015/183871 | 12/2015 |

OTHER PUBLICATIONS

GB Search Report, dated Oct. 2, 2017, in Application No. GB1704761.4.

(Continued)

*Primary Examiner* — Lore R Jarrett
(74) *Attorney, Agent, or Firm* — Illumina, Inc.

(57) ABSTRACT

A system may include a flow cell to support analytes of interest; a selector valve coupled to the flow cell to select a flow path through the flow cell from a plurality of flow paths; a pump coupled to the flow cell to displace fluids through the selected flow path during an analysis operation; and control circuitry coupled to the selector valve to command the selector valve to select the selected flow path.

18 Claims, 16 Drawing Sheets

(52) U.S. Cl.
CPC ... *B01L 3/502715* (2013.01); *B01L 2200/027* (2013.01); *B01L 2200/143* (2013.01); *B01L 2200/16* (2013.01); *B01L 2300/0819* (2013.01); *B01L 2300/0877* (2013.01); *B01L 2300/0883* (2013.01); *B01L 2400/0478* (2013.01); *B01L 2400/0622* (2013.01); *B01L 2400/0644* (2013.01)

(58) Field of Classification Search
CPC ..... B01L 2300/0627; B01L 2300/0867; F16K 99/0028; F16K 27/003; G05D 16/2066; G01N 27/414; G01N 35/04; G01N 15/0637; G01N 15/0656; G01N 27/4145; G01N 35/08; G01N 33/5308; G01N 27/3275; G01N 2015/0065; G01N 33/48721; F04B 53/10
See application file for complete search history.

(56) References Cited

U.S. PATENT DOCUMENTS

| | | | |
|---|---|---|---|
| 2003/0095897 A1* | 5/2003 | Grate | B03C 1/00 422/186 |
| 2010/0024527 A1* | 2/2010 | LaMarr | B01D 15/14 73/61.56 |
| 2010/0111768 A1 | 5/2010 | Banerjee et al. | |
| 2013/0260372 A1 | 10/2013 | Buermann et al. | |
| 2015/0045234 A1* | 2/2015 | Stone | B01L 3/502738 506/2 |
| 2016/0047805 A1 | 2/2016 | Quinn | |

OTHER PUBLICATIONS

PCT/US2017/067838, International Search Report and Written Opinion dated Apr. 23, 2018, 14 pages.

* cited by examiner

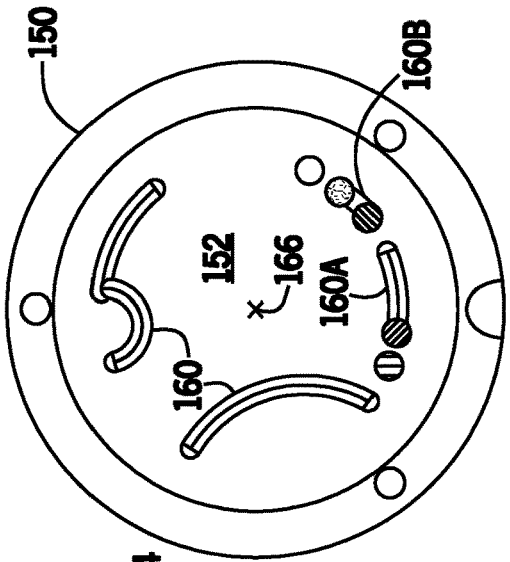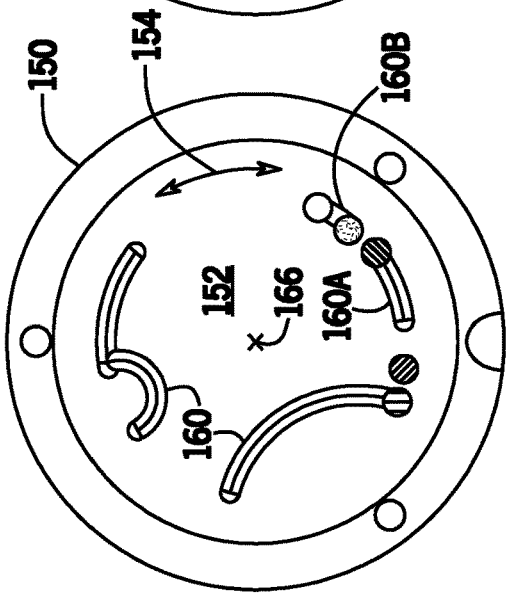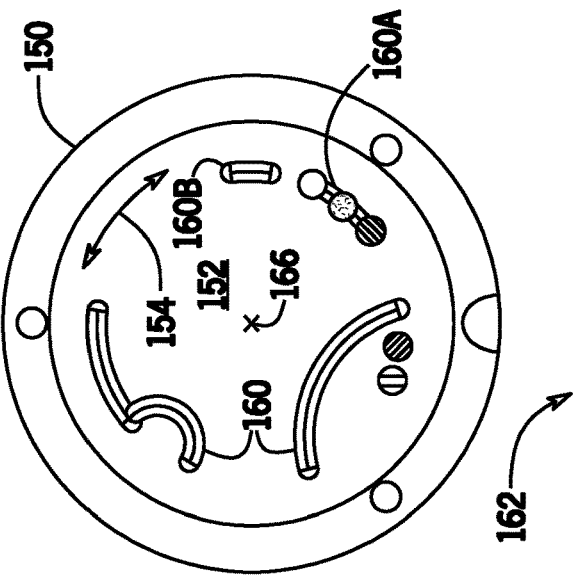

COMMON LINE SELECTOR VALVE FOR A SYSTEM

CROSS-REFERENCE TO RELATED APPLICATIONS

This application claims benefit of priority under to British (GB) Patent Application No. 1704761.4, filed Mar. 24, 2017, which claims benefit of priority to U.S. Patent Application No. 62/442,677, filed Jan. 5, 2017, as well as benefit of priority under 35 U.S.C. § 119(e) to U.S. Patent Application No. 62/442,677, filed Jan. 5, 2017, both of which are hereby incorporated by reference herein in their entireties.

BACKGROUND

Instruments have been developed and continue to evolve for sequencing molecules of interest, particularly DNA, RNA and other biological samples. In advance of sequencing operations, samples of the molecules of interest are prepared in order to form a library which will be mixed with reagents and ultimately introduced into a flow cell where individual molecules will attach at sites and be amplified to enhance detectability. The sequencing operation, then, includes repeating a cycle of steps to bind the molecules at the sites, tag the bound components, image the components at the sites, and process the resulting image data.

In such sequencing systems, fluidic systems (or subsystems) provide the flow of substances (e.g., the reagents) under the control of a control system, such as a programmed computer and appropriate interfaces.

SUMMARY

Details of one or more implementations of the subject matter described in this specification are set forth in the accompanying drawings and the description below. Other features, aspects, and advantages will become apparent from the description, the drawings, and the claims.

In some implementations, a system may be provided that includes: a plurality of flow paths to fluidically connect with a flow cell to support analytes of interest when the flow cell is mounted in the system; a flow path selector valve coupled to the flow paths, the flow path selector valve to select between the flow paths; a pump to fluidically connect with the flow cell when the flow cell is mounted in the system and to displace fluids through one of the flow paths selected by the flow path selector valve during an analysis operation; and control circuitry operatively coupled to the flow path selector valve, the control circuitry having one or more processors and a memory to store, or storing, computer-executable instructions which, when executed by the one or more processors, control the one or more processors to command the flow path selector valve to select the selected flow path.

In some implementations of the system, the plurality of flow paths may include a first flow path to provide fluid flow through a first channel of the flow cell and a second flow path to provide fluid flow through a second channel of the flow cell, in which the second flow path is different from the first flow path.

In some implementations of the system, the plurality of flow paths may include a third flow path that includes both the first and the second flow paths.

In some implementations of the system, the flow path selector valve may be further fluidically coupled to a bypass line that bypasses the flow cell when the flow cell is mounted in the system, and the flow path selector valve may also be controllable to select the bypass line rather than the flow paths.

In some implementations of the system, the control circuitry may automatically command the flow path selector valve to, during the analysis operation, select the selected flow path based upon an analysis protocol.

In some implementations of the system, the system may further include a reagent selector valve positioned fluidically upstream of the flow path selector valve, the reagent selector valve to select a reagent from a plurality of reagents and to direct the selected reagent to an inlet of the flow path selector valve.

In some implementations of the system, the system may include one or more manifolds to fluidically connect the flow cell with the flow path selector valve when the flow cell is mounted in the system, and the one or more manifolds may be fluidically interposed between the flow path selector valve and the flow cell when the flow cell is mounted in the system.

In some implementations of the system, the pump may include a syringe pump located fluidically downstream of the flow cell.

In some implementations, a system may be provided that includes: a reagent selector valve to select a reagent from a plurality of reagents in accordance with an analysis protocol; a flow cell to support analytes of interest; a flow path selector valve fluidically interposed between the reagent selector valve and the flow cell, the flow path selector valve to select a flow path through the flow cell from a plurality of flow paths through the flow cell, and to direct the selected reagent through the selected flow path in accordance with the analysis protocol; a pump that is fluidically connected with the flow cell, the pump to displace the selected reagent through the selected flow path in accordance with the analysis protocol; and control circuitry operatively coupled to the flow path selector valve, the control circuitry having one or more processors and a memory to store, or storing, computer-executable instructions which, when executed by the one or more processors, control the one or more processors to cause the flow path selector valve to select the selected flow path.

In some implementations of the system, the plurality of flow paths may include a first flow path through one channel of the flow cell and a second flow path through a second channel of the flow cell, in which the second flow path is different from the first flow path.

In some implementations of the system, the plurality of flow paths may include a third flow path that includes both the first and the second flow paths.

In some implementations of the system, the flow path selector valve may be further fluidically connected with a bypass line that bypasses the flow cell, and the flow path selector valve may be further controllable to select the bypass line rather than a flow path through the flow cell.

In some implementations of the system, the system may include one or more manifolds fluidically coupled between the selector valve and the flow cell to engage the flow cell with the selector valve when the flow cell is mounted in a sequencing system.

In some implementations, a method may be provided that includes: controlling a flow path selector valve fluidly upstream of a flow cell to select a flow path through the flow cell from a plurality of flow paths through the flow cell and displacing a reagent through the selected flow path in accordance with an analysis protocol, in which the plurality of flow paths includes a first flow path through one channel of the flow cell, a second flow path through a second channel of the flow cell, and a third flow path that includes both the first and the second flow paths, wherein the second flow path is different from the first flow path.

In some implementations of the method, the method may further include controlling a reagent selector valve fluidically connected with the flow path selector valve, the reagent selector valve to select different reagents from a plurality of reagents for displacement through the flow path selector valve and the flow cell in accordance with the analysis protocol, in which the flow path selector valve may be fluidically interposed between the reagent selector valve and the flow cell.

In some implementations of the method, the method may further include commanding changes in positions of the flow path selector valve, the reagent selector valve, or the flow path selector valve and the reagent selector valve during successive cycles of the analysis protocol.

In some implementations of the method, the method may further include commanding the flow path selector valve to select a bypass line that bypasses the flow cell rather than a flow path through the flow cell.

In some implementations of the method, the method may further include mounting the flow cell in a sequencing system to fluidically connect the flow cell with a plurality of manifolds fluidically interposed between the flow path selector valve and the flow cell to fluidically connect the flow cell with the flow path selector valve, in which the mounting of the flow cell is performed prior to displacing the reagent.

In some implementations of the method, the reagent may be displaced through the selected flow path by a pump positioned downstream of the flow cell.

In some such implementations of the method, the pump may include or be a syringe pump.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIGS. 8A through 8F are cross-sectional plan views of different configurations of an implementation of the common line selector valve of the sequencing system of FIG. 1, the different configurations demonstrating different port combinations of the valve;

DETAILED DESCRIPTION

Figure 1:
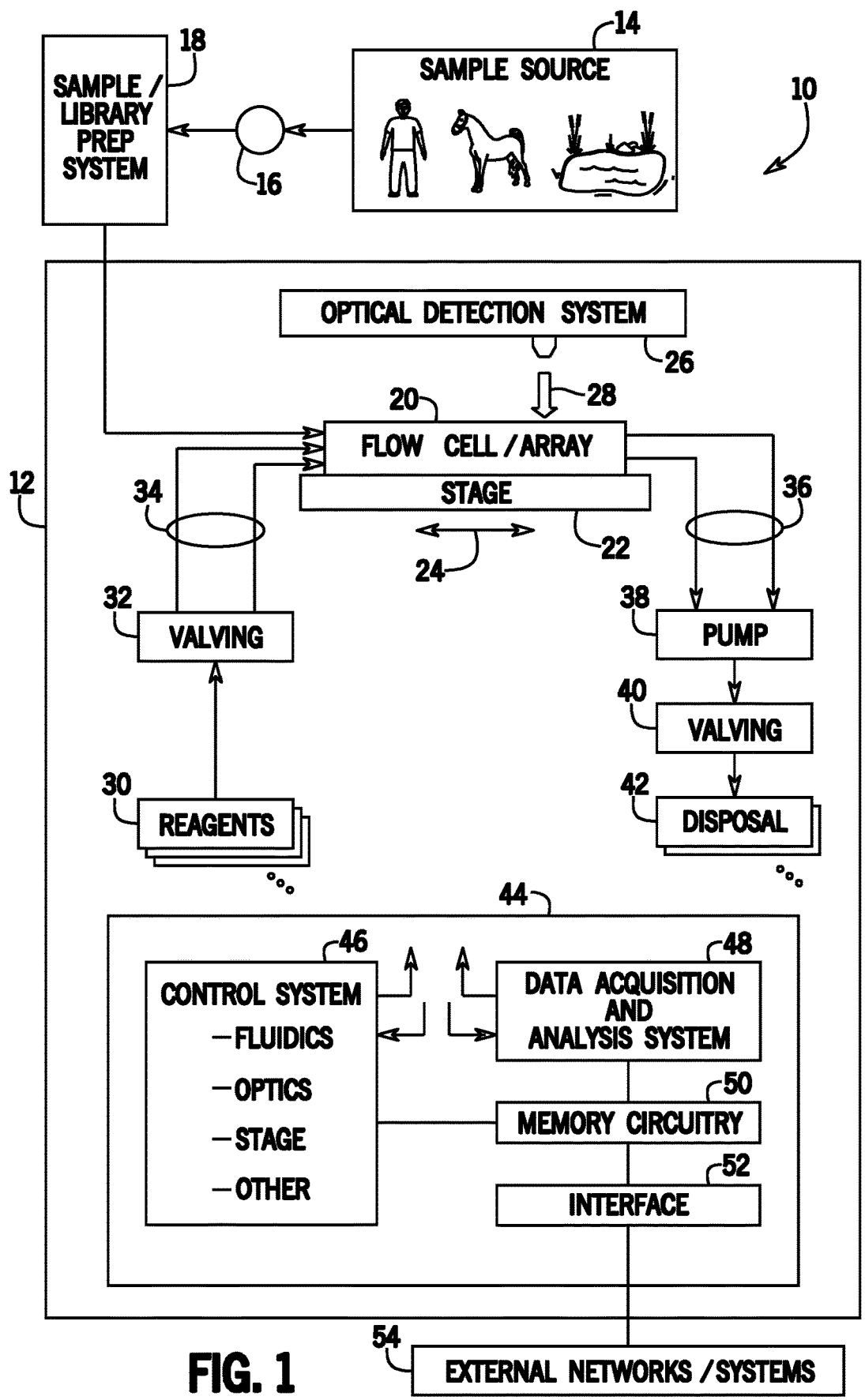
FIG. 1 is a diagrammatical overview of an example sequencing system in which the disclosed techniques may be employed.

FIG. 1 illustrates an implementation of a sequencing system 10 configured to process molecular samples that may be sequenced to determine their components, the component ordering, and generally the structure of the sample. The system includes an instrument 12 that receives and processes a biological sample. A sample source 14 provides the sample 16 which in many cases will include a tissue sample. The sample source may include, for example, an individual or subject, such as a human, animal, microorganism, plant, or other donor (including environmental samples), or any other subject that includes organic molecules of interest, the sequence of which is to be determined. Of course, the system may be used with samples other than those taken from organisms, including synthesized molecules. In many cases, the molecules will include DNA, RNA, or other molecules having base pairs the sequence of which may define genes and variants having particular functions of ultimate interest.

The sample 16 is introduced into a sample/library preparation system 18. This system may isolate, break, and otherwise prepare the sample for analysis. The resulting library includes the molecules of interest in lengths that facilitate the sequencing operation. The resulting library is then provided to the instrument 12 where the sequencing operation is performed. In practice, the library, which may sometimes be referred to as a template, is combined with reagents in an automated or semi-automated process, and then introduced to the flow cell prior to sequencing.

In the implementation illustrated in FIG. 1, the instrument includes a flow cell or array 20 that receives the sample library. The flow cell includes one or more fluidic channels that allow for sequencing chemistry to occur, including attachment of the molecules of the library, and amplification at locations or sites that can be detected during the sequencing operation. For example, the flow cell/array 20 may include sequencing templates immobilized on one or more surfaces at the locations or sites. A "flow cell" may include a patterned array, such as a microarray, a nanoarray, and so forth. In practice, the locations or sites may be disposed in a regular, repeating pattern, a complex non-repeating pattern, or in a random arrangement on one or more surfaces of a support. To enable the sequencing chemistry to occur, the flow cell also allows for introduction of substances, such as including various reagents, buffers, and other reaction media, that are used for reactions, flushing, and so forth. The substances flow through the flow cell and may contact the molecules of interest at the individual sites.

In the instrument the flow cell 20 is mounted on a movable stage 22 that, in this implementation, may be moved in one or more directions as indicated by reference numeral 24. The flow cell 20 may, for example, be provided in the form of a removable and replaceable cartridge that may interface with ports on the movable stage 22 or other components of the system in order to allow reagents and other fluids to be delivered to or from the flow cell 20. The stage is associated with an optical detection system 26 that can direct radiation or light 28 to the flow cell during sequencing. The optical detection system may employ various methods, such as fluorescence microscopy methods, for detection of the analytes disposed at the sites of the flow cell. By way of non-limiting example, the optical detection system 26 may employ confocal line scanning to produce progressive pixilated image data that can be analyzed to locate individual sites in the flow cell and to determine the type of nucleotide that was most recently attached or bound to each site. Other imaging techniques may also suitably be employed, such as techniques in which one or more points of radiation are scanned along the sample or techniques employing "step and shoot" imaging approaches. The optical detection system 26 and the stage 22 may cooperate to maintain the flow cell and detection system in a static relationship while obtaining an area image, or, as noted, the flow cell may be scanned in any suitable mode (e.g., point scanning, line scanning, "step-and-shoot" scanning).

While many different technologies may be used for imaging, or more generally for detecting the molecules at the sites, presently contemplated implementations may make use of confocal optical imaging at wavelengths that cause excitation of fluorescent tags. The tags, excited by virtue of their absorption spectrum, return fluorescent signals by virtue of their emission spectrum. The optical detection system 26 is configured to capture such signals, to process pixelated image data at a resolution that allows for analysis of the signal-emitting sites, and to process and store the resulting image data (or data derived from it).

In a sequencing operation, cyclic operations or processes are implemented in an automated or semi-automated fashion in which reactions are promoted, such as with single nucleotides or with oligonucleotides, followed by flushing, imaging and de-blocking in preparation for a subsequent cycle. The sample library, prepared for sequencing and immobilized on the flow cell, may undergo a number of such cycles before all useful information is extracted from the library. The optical detection system may generate image data from scans of the flow cell (and its sites) during each cycle of the sequencing operation by use of electronic detection circuits (e.g., cameras or imaging electronic circuits or chips). The resulting image data may then be analyzed to locate individual sites in the image data, and to analyze and characterize the molecules present at the sites, such as by reference to a specific color or wavelength of light (a characteristic emission spectrum of a particular fluorescent tag) that was detected at a specific location, as indicated by a group or cluster of pixels in the image data at the location. In a DNA or RNA sequencing application, for example, the four common nucleotides may be represented by distinguishable fluorescence emission spectra (wavelengths or wavelength ranges of light). Each emission spectrum, then, may be assigned a value corresponding to that nucleotide. Based upon this analysis, and tracking the cyclical values determined for each site, individual nucleotides and their orders may be determined for each site. These sequences may then be further processed to assemble longer segments including genes, chromosomes, and so forth. As used in this disclosure the terms "automated" and "semi-automated" mean that the operations are performed by system programming or configuration with little or no human interaction once the operations are initiated, or once processes including the operations are initiated.

In the illustrated implementation, reagents 30 are drawn or aspirated into the flow cell through valving 32. The valving may access the reagents from recipients or vessels in which they are stored, such as through pipettes or sippers (not shown in FIG. 1). The valving 32 may allow for selection of the reagents based upon a prescribed sequence of operations performed. The valving may further receive commands for directing the reagents through flow paths 34 into the flow cell 20. Exit or effluent flow paths 36 direct the used reagents from the flow cell. In the illustrated implementation, a pump 38 serves to move the reagents through the system. The pump may also serve other useful functions, such as measuring reagents or other fluids through the system, aspirating air or other fluids, and so forth. Additional valving 40 downstream of pump 38 allows for appropriately directing the used reagent to disposal vessels or recipients 42.

The instrument further includes a range of circuitry that aids in commanding the operation of the various system components, monitoring their operation by feedback from sensors, collecting image data, and at least partially processing the image data. In the implementation illustrated in FIG. 1, a control/supervisory system 44 includes a control system 46 and a data acquisition and analysis system 48. Both systems will include one or more processors (e.g., digital processing circuits, such as microprocessors, multi-core processors, FPGA's, or any other suitable processing circuitry) and associated memory circuitry 50 (e.g., solid state memory devices, dynamic memory devices, on and/or off-board memory devices, and so forth) that may store machine-executable instructions for controlling, for example, one or more computers, processors, or other similar logical devices to provide certain functionality. Application-specific or general purpose computers may at least partially make up the control system and the data acquisition and analysis system. The control system may include, for example, circuitry configured (e.g., programmed) to process commands for fluidics, optics, stage control, and any other useful functions of the instrument. The data acquisition and analysis system 48 interfaces with the optical detection system to command movement of the optical detection system or the stage, or both, the emission of light for cyclic detection, receiving and processing of returned signals, and so forth. The instrument may also include various interfaces as indicated at reference 52, such as an operator interface that permits control and monitoring of the instrument, transfer of samples, launching of automated or semi-automated sequencing operations, generation of reports, and so forth. Finally, in the implementation of FIG. 1, external networks or systems 54 may be coupled to and cooperate with the instrument, for example, for analysis, control, monitoring, servicing, and other operations.

It may be noted that while a single flow cell and fluidics path, and a single optical detection system are illustrated in FIG. 1, in some instruments more than one flow cell and fluidics path may be accommodated. For example, in a presently contemplated implementation, two such arrangements are provided to enhance sequencing and throughput. In practice, any number of flow cells and paths may be provided. These may make use of the same or different reagent receptacles, disposal receptacles, control systems, image analysis systems, and so forth. Where provided, the multiple fluidics systems may be individually controlled or controlled in a coordinated fashion.

Figure 2:
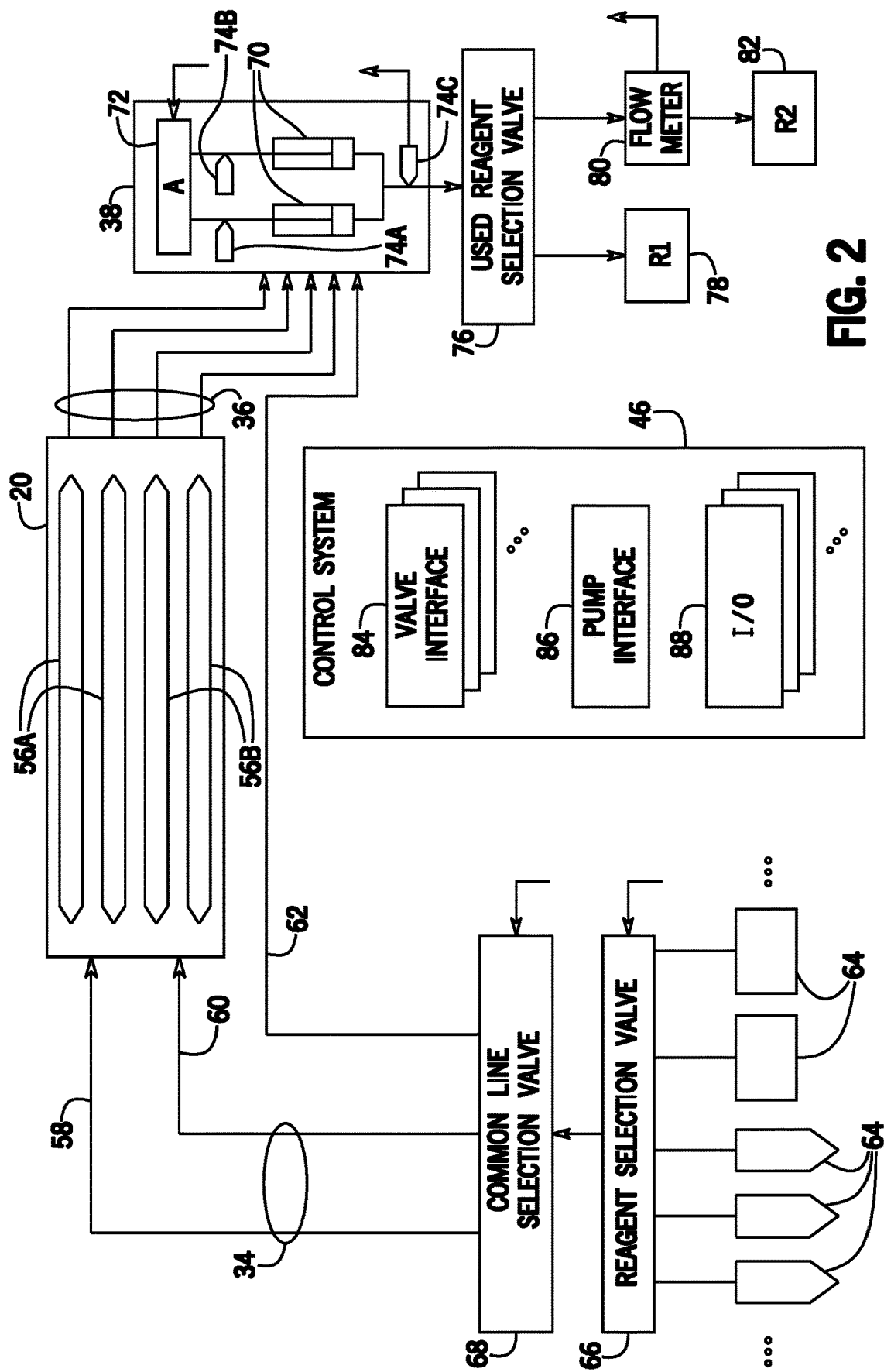
FIG. 2 is a diagrammatical overview of one implementation of the fluidic system of the example sequencing system of FIG. 1.

FIG. 2 illustrates an example fluidic system of the sequencing system of FIG. 1. In the implementation illustrated, the flow cell 20 includes a series of pathways or lanes 56A and 56B which may be grouped in pairs for receiving fluid substances (e.g., reagents, buffers, reaction media) during analysis (e.g., including sequencing) operations. The lanes 56A are coupled to a common line 58 (a first common line), while the lanes 56B are coupled to a second common line 60. A bypass line 62 is also provided to allow fluids to bypass the flow cell without entering it. As noted above, a series of vessels or recipients 64 allow for the storage of reagents and other fluids that may be utilized during the analysis operation. A reagent selector valve (RSV) 66 is coupled to a motor or actuator (not shown) to allow selection of one or more of the reagents to be introduced into the flow cell. Selected reagents are then advanced to a common line selector valve (CLSV) 68 which similarly includes a motor (not shown). The common line selector valve may be commanded to select one or more of the common lines 58 and 60, or both common lines, to cause the reagents 64 to flow to the lanes 56A and/or 56B in a controlled fashion, or the bypass line 62 to flow one or more of the reagents through the bypass line.

Used reagents exit the flow cell through lines coupled between the flow cell and the pump 38. In the illustrated implementation, the pump includes a syringe pump having a pair of syringes 70 that are controlled and moved by an actuator 72 to aspirate the reagents and other fluids and to eject the reagents and fluids during different operations of the testing, verification and analysis (e.g., sequencing) cycles. The pump assembly may include various other parts and components, including valving, instrumentation, actuators, and so forth (not shown). In the illustrated implementation, pressure sensors 74A and 74B sense pressure on inlet lines of the pump, while a pressure sensor 74C is provided to sense pressures output by the syringe pump.

Fluids used by the system enter a used reagent selector valve 76 from the pump. This valve allows for selection of one of multiple flow paths for used reagents and other fluids. In the illustrated implementation, a first flow path leads to a first used reagent receptacle 78, while a second flow path leads through a flow meter 80 a second used reagent receptacle 82. Depending upon the reagents used, it may be advantageous to collect the reagents, or certain of the reagents in separate vessels for disposal, and the used reagent selector valve 76 allows for such control.

It should be noted that valving within the pump assembly may allow for various fluids, including reagents, solvents, cleaners, air, and so forth to be aspirated by the pump and injected or circulated through one or more of the common lines, the bypass line, and the flow cell. Moreover, as noted above, in a presently contemplated implementation, two parallel implementations of the fluidics system shown in FIG. 2 are provided under common control. Each of the fluidics systems may be part of a single analysis instrument, and may carry out functions including sequencing operations on different flow cells and sample libraries in parallel.

The fluidics system operates under the command of control system 46 which implements prescribed protocols for testing, verification, analysis (e.g., including sequencing), and so forth. The prescribed protocols will be established in advance and include a series of events or operations for activities such as aspirating reagents, aspirating air, aspirating other fluids, ejecting such reagents, air and fluids, and so forth. The protocols will allow for coordination of such fluidic operations with other operations of the instrument, such as reactions occurring in the flow cell, imaging of the flow cell and its sites, and so forth. In the illustrated implementation, the control system 46 employs one or more valve interfaces 84 which are configured to provide command signals for the valves, as well as a pump interface 86 configured to command operation of the pump actuator. Various input/output circuits 88 may also be provided for receiving feedback and processing such feedback, such as from the pressure sensors 74A-C and flow meter 80.

Figure 3:
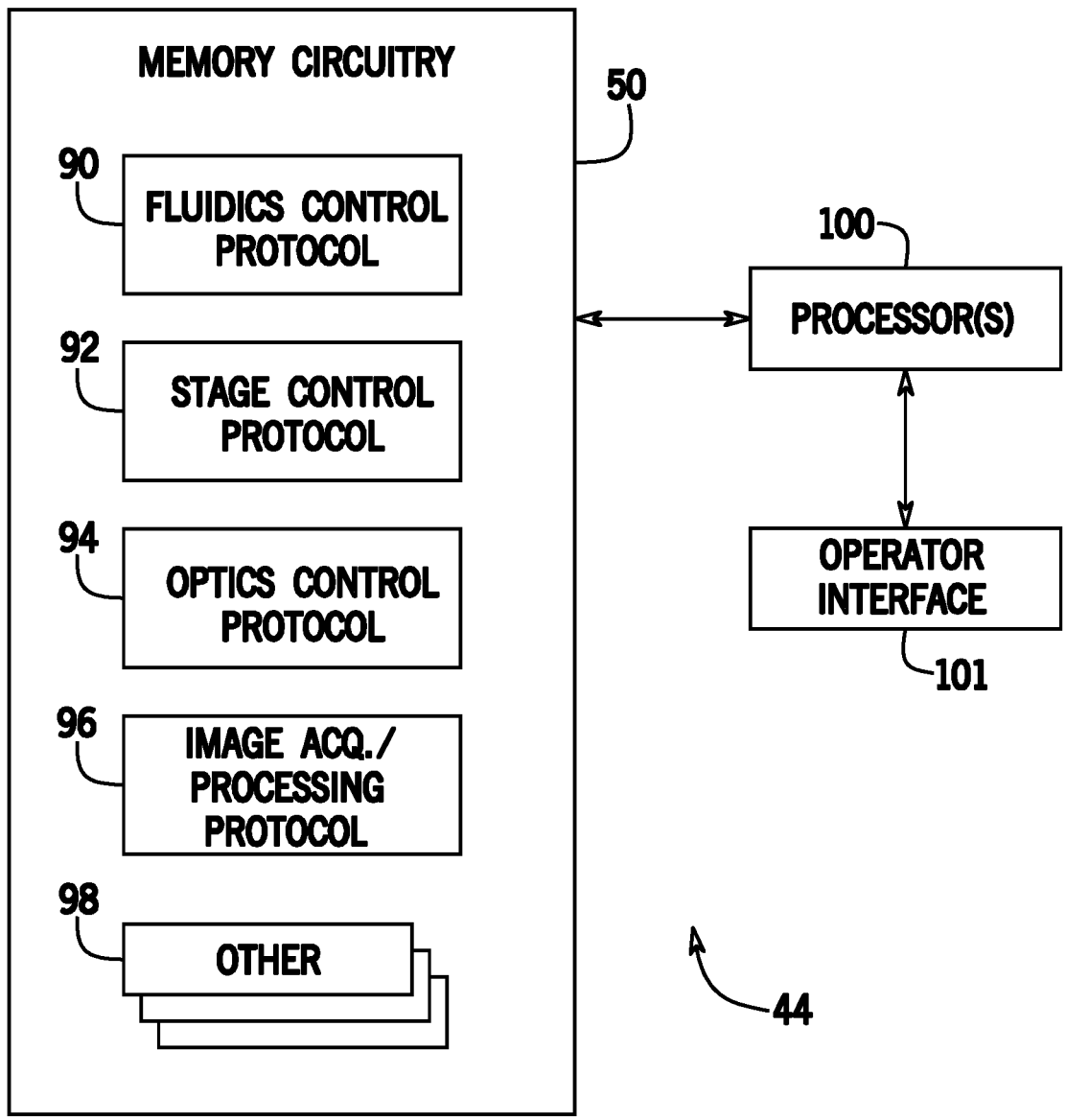
FIG. 3 is a diagrammatical overview of an example processing and control system of the example sequencing system of FIG. 1.

FIG. 3 illustrates certain functional components of the control/supervisory system 44. As illustrated, the memory circuitry 50 stores prescribed routines that are executed during testing, commissioning, troubleshooting, servicing, and analysis operations. Many such protocols and routines may be implemented and stored in the memory circuitry, and these may be updated or altered from time to time. As illustrated in FIG. 3, these may include a fluidics control protocol 90 for controlling the various valves, pumps, and any other fluidics actuators, as well as for receiving and processing feedback from fluidics sensors, such as valves, and flow and pressure sensors. A stage control protocol 92 allows for moving the flow cell as desired, such as during imaging. An optics control protocol 94 allows for commands to be issued to the imaging components to illuminate portions of the flow cell and to receive returned signals for processing. An image acquisition and processing protocol 96 allows for the image data to be at least partially processed for extraction of useful data for analysis. Other protocols and routines may be provided in the same or different memory circuitry as indicated by reference 98. In practice, the memory circuitry may be provided as one or more memory devices, such as both volatile and non-volatile memory. This memory may be within the instrument, and some may be off-board.

One or more processors 100 access the stored protocols and implement them on the instrument. As noted above, the processing circuitry may be part of application-specific computers, general-purpose computers, or any suitable hardware, firmware and software platform. The processors and the operation of the instrument may be commanded by human operators via an operator interface 101. The operator interface may allow for testing, commissioning, troubleshooting, and servicing, as well as for reporting any issues that may arise in the instrument. The operator interface may also allow for launching and monitoring analysis operations.

Figure 4:
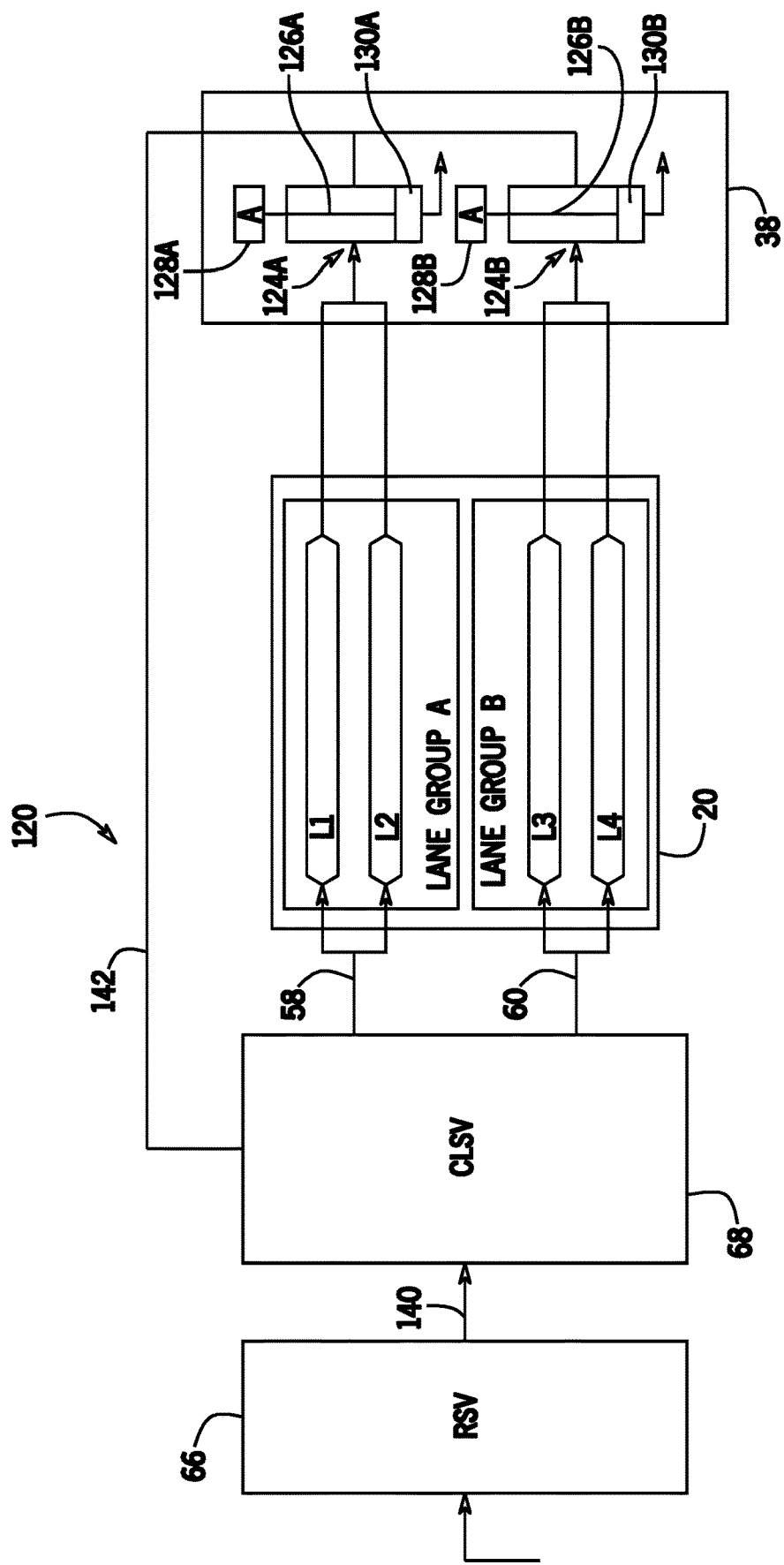
FIG. 4 is a diagrammatical overview of another implementation of a portion of a fluidic system for the example sequencing system of FIG. 1.

FIG. 4 illustrates a portion of the fluidic system 120 for an implementation of the instrument 12, wherein the arrows are indicative of a capability to flow substances (e.g., reagents, buffers, analytes) through the various illustrated flow paths during sample analysis. For the implementation illustrated in FIG. 4, the flow cell 20 includes two lane groups, denoted as lane group A and lane group B. Other implementations of the flow cell 20 may include a different number of lane groups, such as more than two lane groups. The flow cell 20 may, in still further implementations, include only one lane group. The flow cell 20 may be a removable and/or replaceable item of the analysis system.

Each of the two illustrated lane groups A and B includes two respective fluidic channels or lanes, denoted as lanes L1, L2, L3, and L4 in FIG. 4. In this respect, the lane groups A and B may be referred to as "lane pairs," as they each include two respective lanes. For the illustrated implementation, the flow cell 20 is designed to be operated such that substances (e.g., fluids) can be motivated through the lane groups A and B in the direction indicated by the arrows during an analysis protocol. Other protocols for testing and so forth may flow certain substances in different directions.

Additionally, the pump 38 of the fluidic system illustrated in FIG. 4 includes multiple syringe pumps 124 (e.g., syringe pumps 124A and 124B). As illustrated, the syringe pumps 124 each include one or more respective syringes 126 (e.g., syringe 126A corresponding to lane group A and syringe 126B corresponding to lane group B) that are respectively actuated by actuators 128 (e.g., actuators 128A and 128B). The illustrated syringe pumps 124 also include valving 130 (e.g., valving 130A and 130B), which enable the syringe pumps to push or pull fluids into and out of different orifices or ports of the pumps 124.

The manner in which fluids are advanced through the flow cell 20 is coordinated, completely or in part, through control of the syringe pumps 124, the RSV 66, and the CLSV 68. As set forth above with respect to FIG. 2, the RSV 66 is fluidically coupled to sources of various reagents, and allows selective fluidic coupling between the sources of the reagents and the CLSV 68. As an example, an RSV to CLSV common line 140 may fluidically couple a reagent outlet port of the RSV 66 with a common line inlet port of the CLSV 68, and the RSV to CLSV common line 140 is designed to flow various fluids (e.g., reagents) between the RSV 66 and the CLSV 68.

As discussed in further detail herein, the CLSV 68 allows selective fluidic coupling between the reagent selected at the RSV 66 (e.g., via a selected reagent port) and various flow paths within the flow cell 20. In this way, the CLSV 68 is coupled to the flow cell 20 to select a flow path for fluids through the flow cell 20 from a plurality of flow paths, and the plurality of flow paths includes a first flow path through one channel of the flow cell, and a second flow path through a second channel of the flow cell different from the first flow path. In certain implementations, the plurality of flow paths includes a third flow path that includes both the first and the second flow paths. In the illustrated implementation, this means that the CLSV 68 is configured to, among other things, allow selected fluidic coupling between the RSV 66 and either or both of lane group A and lane group B (a first lane group and a second lane group, respectively), and in certain implementations other fluid paths. In this way, the CLSV 68 allows individual addressing of each lane group, or lane pair, of the flow cell 20. The CLSV 68 also allows selective fluidic coupling between the RSV 66 and a bypass line 142, which may be useful to prime the use of a reagent without aspirating fluid through the flow cell 20, may be useful for certain testing protocols, and other protocols. As used herein, the term "fluidic coupling" is intended to denote coupling between flow paths allowing fluid flow between the flow paths. Accordingly, selected or selective fluidic coupling denotes the capability to selectively couple flow paths to allow fluids to flow between them, the flow paths otherwise (when not fluidically coupled) being fluidically isolated from one another (fluids cannot flow between them). During analysis operations, the control circuitry automatically commands the CLSV 68 (e.g., via a motor) to select the selected flow path based upon an analysis protocol. For example, a flow cell may be mounted in the sequencing system, and one or more manifolds (e.g., a plurality of manifolds) may engage the flow cell 20 with the CLSV 68 when the flow cell 20 is appropriately mounted. The control circuitry may perform certain diagnostics to ensure appropriate fluid connections have been established, may perform certain pre-analysis (e.g., pre-sequencing) operations including reagent priming of the fluidic system 120, and may then commence various analysis (e.g., including sequencing) protocols.

Figure 5:
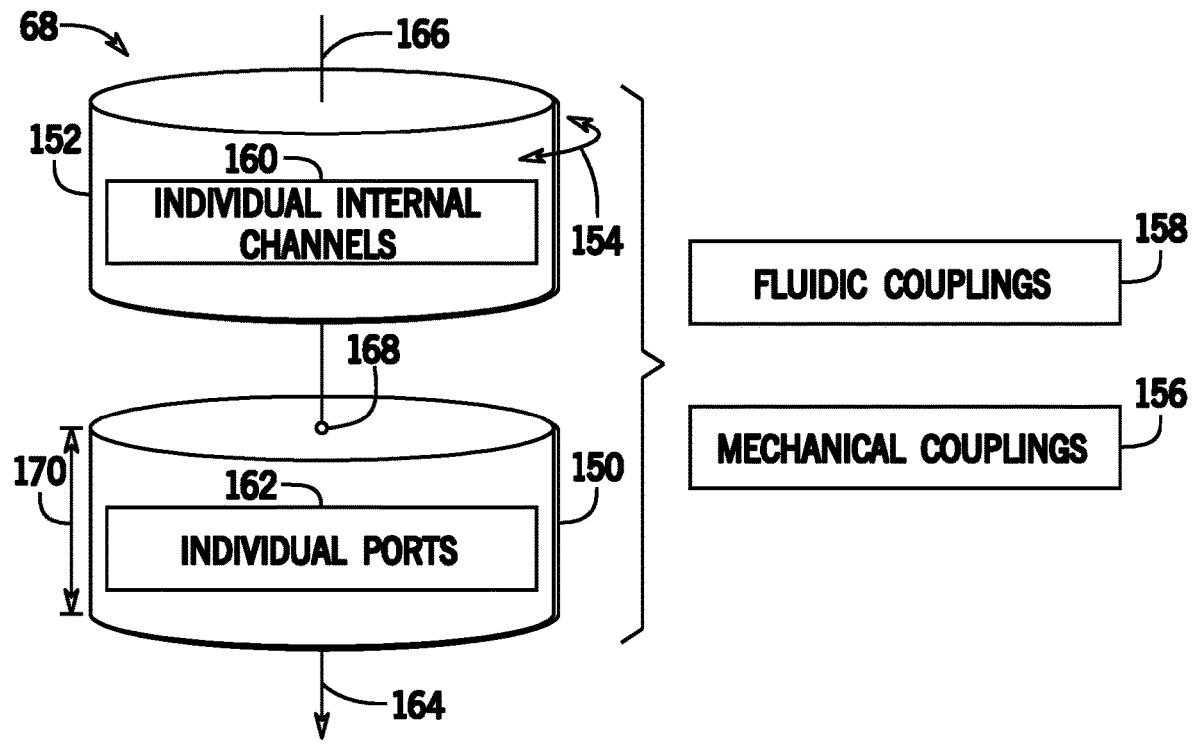
FIG. 5 is a schematic exploded view of an implementation of a common line selector valve used in the sequencing system of FIG. 1.

Selective fluidic coupling using the CLSV 68 as set forth above may be accomplished using certain physical features of the valve 68, an implementation of which is schematically illustrated in FIG. 5. As shown, the CLSV 68 includes a stationary portion 150 and a movable portion 152, which are shown as separated from one another. When assembled, the stationary portion 150 and the movable portion 152 are positioned directly against one another in a manner that prevents fluid leakage between their respective fluidic components (e.g., fluid ports, fluid channels). The movable portion 152 is configured to move (e.g., translate, rotate), as shown by arrow 154, relative to the stationary portion 150 to form various fluidic connections between their respective fluidic components. Whether the movable portion 152 is translated, rotated, or both, will depend on the particular geometrical configuration of the CLSV 68 (e.g., elongated, annular, polygonal), as well as the nature of various mechanical couplings 156 and fluidic couplings 158 of the valve 68. Mechanical couplings 156 of the CLSV 68 may include couplings made by fasteners between the valve 68 and other components of the sequencing system 10, such as a housing of a manifold assembly that includes the valves 66, 68, and various fluid paths as described herein. The mechanical couplings 156 may also include couplings made between the movable portion 152 and an actuator, such as a motor, and between the movable portion 152 and the stationary portion 150.

The fluidic couplings 158 may be dynamic, in that the couplings may be adjusted, closed, opened, formed, blocked, and so on. The fluidic couplings 158 may include couplings to various lines (e.g., the flow paths 34 of FIG. 2), such as common lines 58 and 60, as well as the RSV to CLSV common line 140 of FIG. 4. In certain implementations, the fluidic couplings may include one or more manifolds that operate to fluidically couple the CLSV 68 to the flow cell 20, for example when the flow cell 20 is mounted in the sequencing system.

In accordance with present implementations, movement 154 of the movable portion 152 relative to the stationary portion 150 adjusts overlap between individual channels 160 and individual ports 162 to produce various combinations of fluidically coupled ports. The various combinations of fluidically coupled ports are used to determine the flow path of fluids through the flow cell 20.

In the illustrated implementation, the individual channels 160 are a part of (e.g., are formed in) the movable portion 152 and the individual ports 162 are a part of the (e.g., are formed in) the stationary portion 150. However, other implementations of the CLSV 68 may have some or all the individual ports 162 in the movable portion 152 and some or all the individual channels 160 in the stationary portion 150. Formation of the individual channels 160 and individual ports 162 in their respective portions may be accomplished, for example, by subtractive manufacturing (e.g., etching, machining, and lithography) or by additive manufacturing. The material or materials of the CLSV 68 may be chosen or designed to withstand the fluids normally used during analysis and testing protocols of the system 10 (FIG. 1), for example such that the material or materials do not leech in to the reagents and to prevent crazing or other chemically-induced degradation. In addition, the material or materials of the CLSV 68 may be chosen to have a certain coefficient of friction between the movable and stationary portions 150, 152 to provide sufficient resistance to accidental movement of the movable portion 152, while still allowing the movable portion 152 to freely move under a certain amount of force applied by an actuator or a user.

As shown, the movable portion 152 and the stationary portion 150 include annular geometries that overlap in an axial direction 164. In the illustrated implementation, the overlap is such that a center point 166 of the movable portion 152 and a center point 168 of the stationary portion 150 are substantially aligned along the axial direction 164. Other implementations of the valve 68 may have an arrangement in which the center points 166, 168 are offset from one another, for example due to spatial constraints within a cartridge including the valve 68, certain design considerations, and so forth. Indeed, the movable portion 152 and the stationary portion 150 may not be the same size (e.g., have the same circumference, length, or depth, and may have different geometries (different shapes). For instance, while the movable portion 152 is shown in a stacked relationship relative to the stationary portion 150 in the schematic of FIG. 5, certain implementations of the CLSV 68 may have the movable portion 152 nested within the stationary portion 150 (but also in a stacked relationship).

To produce fluidic couplings using the CLSV 68, certain of the individual ports 162, which extend through a thickness 170 of the stationary portion 150 (e.g., between parallel planar surfaces 172, 174), are aligned in the axial direction 166 with certain of the internal channels 160. The individual ports 162 extend through the stationary portion 150 from surface 172, which is a first side of the stationary portion 150 facing away from the movable portion 152, to surface 174, which is a second side of the stationary portion 150 that faces and directly abuts the movable portion 152. The individual ports 162 are separate and distinct from one another in the stationary portion 150, and may be used to deliver or receive fluids depending on the arrangement of the fluidic couplings 158.

Figure 6:
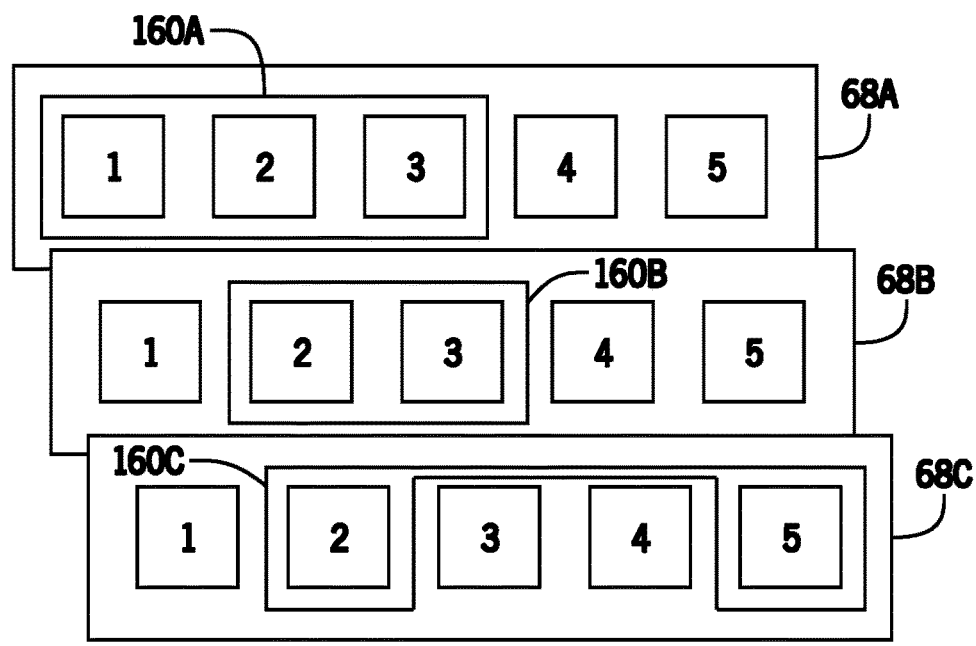
FIG. 6 is a schematic illustrating example port combinations enabled by the common line selector valve of the sequencing system of FIG. 1.

In accordance with present implementations, the individual channels 160 have geometries that allow different combinations of the individual ports 162 to be coupled to one another. This is shown schematically in FIG. 6, which includes different example port combinations of the CLSV 68. As shown, the implementation of the CLSV 68 includes five different ports, though other numbers of ports may be included in other implementations.

As depicted by the example valve configuration 68A, a first fluid channel 160A of the valve 68 fluidically couples ports 1, 2, and 3. As an example, port 2 may be an inlet, and ports 1 and 3 may be lane group outlets (leading to lane groups). Such a configuration may be referred to as a high throughput configuration, where parallel operations (e.g., sequencing operations) are carried out, for example, in the parallel lane groups A and B. In certain testing protocols, for example pressure testing protocols, certain fluids may be advanced in a different flow direction, i.e., from the lane groups A and B, and back through the valve 68 and common line 140.

In the example valve configuration 68B, a second fluid channel 160B of the valve 68 fluidically couples only the ports 2 and 3. In implementations where 2 is a fluid inlet and 3 is a fluid outlet, the CLSV 68 therefore selects a single lane group flow through the flow cell 20. In the valve configuration 68C, a third fluid channel 160C fluidically couples the port 2 and port 5. In such a configuration, the CLSV 68 only allows fluid to flow between these ports, and, when port 5 is fluidically coupled to a line other than a lane group (e.g., a bypass line), does not allow flow to the lane groups of the flow cell 20 and instead bypasses them. Fluidic coupling of the various ports of the CLSV 68 may result in combinations other than the ones shown in FIG. 6, and indeed, any one or a combination of ports may be selected using implementations of the CLSV 68.

Again, different fluidically coupled port combinations may be made by moving the movable portion 152 of the CLSV 68 relative to the stationary portion 150 such that different individual channels 160 of the movable portion 152 align with various combinations of the individual ports 162 of the stationary portion 150. The manner in which the channels 160 may be used to fluidically couple the ports 162 may be further appreciated with reference to FIGS. 7A and 7B, which are cross-sectional elevation views of an implementation of the CLSV 68. In the implementation illustrated in FIGS. 7A and 7B, certain of the ports 162 (e.g., a bypass line port and an air inlet port) are not shown for clarity in the figure. However, it should be appreciated that such ports may be present in different regions of the valve 68.

Figure 7A:
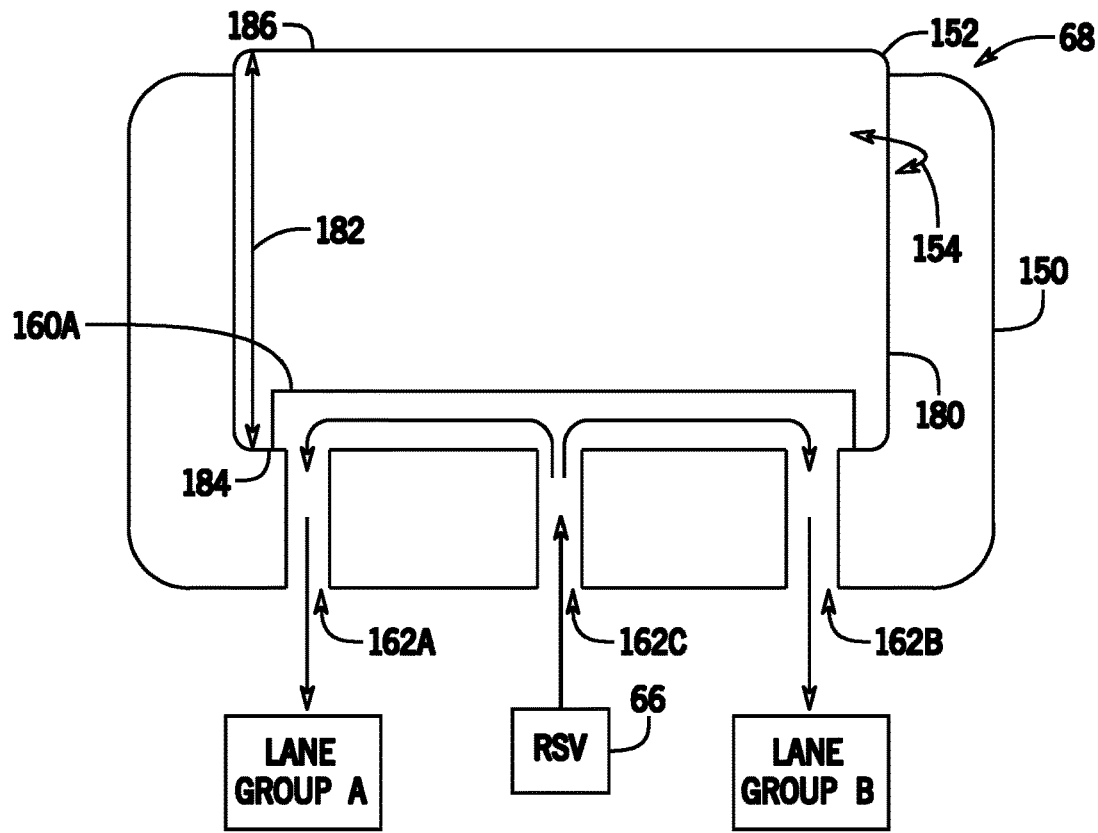
FIGS. 7A and 7B are cross-sectional elevation views of different configurations of an implementation of the common line selector valve of the sequencing system of FIG. 1 and depicting examples of the manner in which fluids may flow through the valve.
Figure 7B:
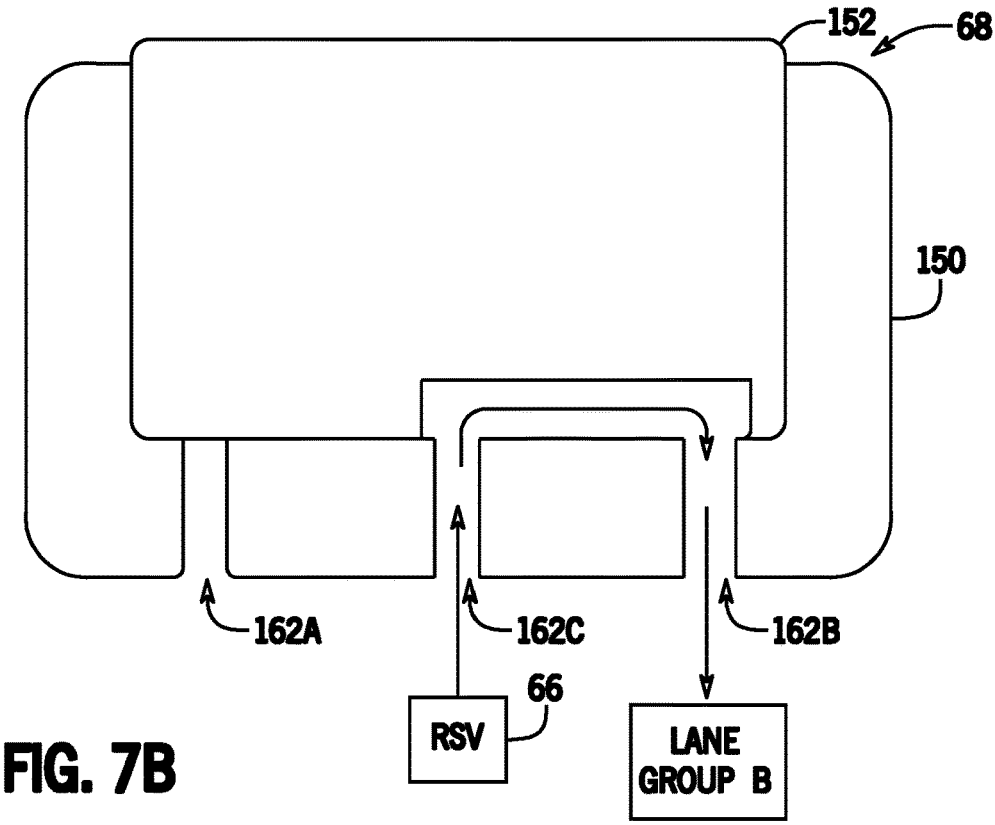

In FIGS. 7A and 7B, the movable portion 152 is nested within a receptacle region 180 of the stationary portion 150, and is rotatable relative to the stationary portion 150. In the depicted implementation, the first channel 160A is axially overlapping with a first port (a lane group A port 162A), a second port (a lane group B port 162B), and a third port (an RSV port 162C) to fluidically couple the ports to one another. In accordance with present implementations and as shown, the channels 160 extend only partially through a thickness 182 of the movable portion 152 (as determined by a distance between parallel surfaces 184, 186, where surface 184 abuts surface 174 of the stationary portion 150 and surface 186 faces away from the stationary portion 150).

Because the movable portion 152 is tightly sealed against the stationary portion 150, fluid only passes between the ports 162A, 162B, and 162C. When substances are advanced into the flow cell 20 (FIG. 4), for example during portions of sequencing protocols, fluid may only flow in the manner depicted by the arrows extending from the port 162C and to the ports 162A and 162B, which is determined by the shape of the first channel 160A. Further, as shown in FIG. 7B, which is an orientation of the CLSV 68 that is produced by rotation of the movable portion 152 relative to FIG. 7A, the movable portion 152 (the body thereof) is firmly sealed against the lane group A port 162A such that fluid does not leave the port 162A. Instead of the first channel 160A being aligned with the ports as in FIG. 7A, in FIG. 7B a second channel 160B is aligned with the ports 162B and 162C, which fluidically connects the two and allows fluid to flow through each port and out of the CLSV 68. As fluid is advanced into the flow cell 20, for example during a sequencing protocol, fluid may flow as shown by the arrows from the RSV 66, through the RSV port 162C, through the second channel 160B, out of the lane group B port 162B, and to the lane group B (e.g., via line 60 of FIGS. 2 and 4).

A number of other fluidic combinations and flow directions may be realized by adjusting the position of the movable portion 152 relative to the stationary portion 150, and by appropriate aspiration using the pump 38. In implementations where the movable portion 152 and the stationary portion 150 are both annular, then, rotation of the movable portion 152 acts to align a particular one of the channels 160, which are arced, with one or more of the ports 162, which are positioned at different circumferential positions of the stationary portion 150. The channels 160 will have different geometries, which generally denotes different shapes but having certain shared parameters (e.g., channel depth as determined by the size of the channels 160 along the thickness 182 of the movable portion 152, channel width as determined by the size of the channels 160 in a radial direction of the movable portion). The different geometries allow the different fluidic connections to be made.

One implementation of the CLSV 68 having ports for the RSV 66, for lane groups A and B, for the bypass line 142, and for air is shown in FIGS. 8A through 8F, which are diagrammatical plan views of the CLSV 68 in various positions or orientations. Different shading or hashing is used to distinguish between the ports 162 of the CLSV 68. It should be appreciated that the series of positions of the CLSV 68 illustrated in FIGS. 8A through 8F may be commanded by the control circuitry of the sequencing system, for example to correspond to certain testing operations, pre-sequencing operations, or sequencing operations.

Figure 8F:
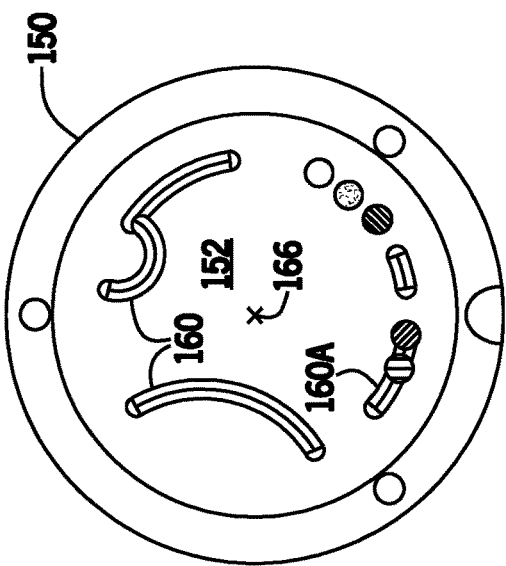
Figure 8E:
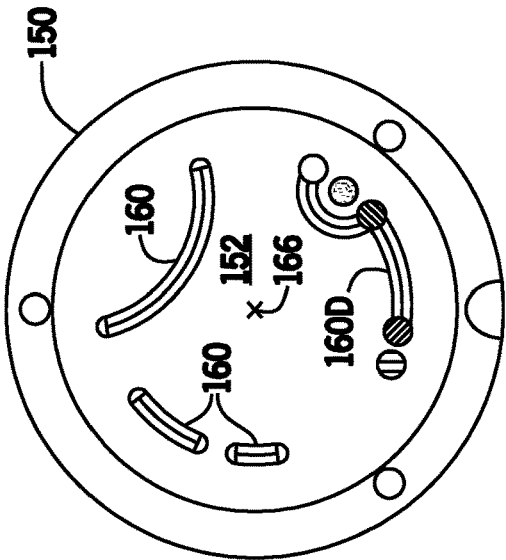

The CLSV 68 illustrated in FIGS. 8A-8F has the movable portion 152 that rotates about the axial direction 164 and that includes the various internal channels 160. Again, the movable portion 152 is firmly sealed against ports 162 such that fluid does not leave a port 162 unless a channel 160 is suitably aligned to enable flow to another port 162. For example, the orientation of the CLSV 68 illustrated in FIG. 8A, referred to hereafter as the "RSV to Lane Groups A & B" position, fluidically couples the RSV port 162C to both the lane group A port 162A and the lane group B port 162B using an implementation of the first channel 160A, which is geometrically designed to overlap axially with the ports 162A, 162B, and 162C to fluidically couple them together. It should be noted that the remaining channels 160 of the CLSV 68, in the position shown in FIG. 8A, are positioned and geometrically designed such that they do not couple other ports 162 of the CLSV 68 together.

Clockwise rotation of the movable portion 152 relative to the stationary portion 150 about the axial direction 164 transitions the CLSV 68 to the position shown in FIG. 8B, which results in a fluid coupling of the lane group A port 162A with the RSV port 162C, referred to hereafter as the "RSV to Lane Group A" position using an implementation of the second channel 160B, which is geometrically designed to overlap axially with the ports 162A and 162C to fluidically couple them together. As shown, the remaining channels 160 of the CLSV 68, in the position shown in FIG. 8B, are positioned and geometrically designed such that they do not couple other ports 162 of the CLSV 68 together. Therefore, although the first channel 160A is fluidically coupled to the lane group B port 162B, the lane group B port 162B remains fluidically isolated from the other ports because the channels 160 are fluidically isolated from one another.

Continuing with clockwise rotation, the CLSV 68 transitions to a configuration shown in FIG. 8C, where the RSV port 162C is fluidically coupled to the lane group B port 162B, referred to hereafter as the "RSV to Lane Group B" position, using the second channel 160B. Because the second channel 160B is appropriately sized to only couple two adjacent ports 162, it may be utilized in several different positions to couple adjacent ports 162. Thus, in accordance with present implementations, one of the channels 160 may be used to produce more than one combination of fluid couplings between ports 162. Here, the remaining ports 162 are once again isolated from other ports 162 due to the positioning and geometric design of the channels 160, in combination with the respective positions of the ports 162.

The orientations illustrated in FIGS. 8A-8C enable the implementation of the fluidic system 120 illustrated in FIG. 4 to operate, as described above, to direct fluids received from the RSV 66 through a single lane group (e.g., lane groups A or B) or both lane groups A and B simultaneously. Further, while described in the context of clockwise rotation, the CLSV 68 may additionally or alternatively be rotated counterclockwise, depending on the current position of the channels 160 and the desired port combination. For instance, starting from the orientation shown in FIG. 8A, the movable portion 152 may be rotated counterclockwise to produce the orientation shown in FIG. 8D.

Figure 8D:
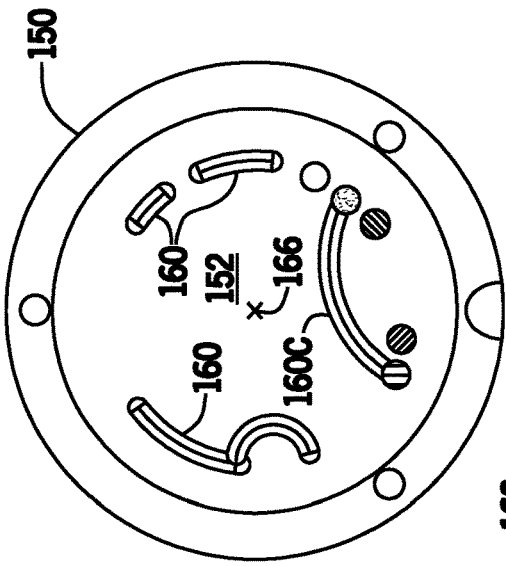

The orientation illustrated in FIG. 8D enables the implementation of the fluidic system 120 to flow fluids between the RSV 66 and the bypass line 142, and is referred to hereafter as the "RSV to Bypass" position. In this position, an implementation of the third channel 160C fluidically couples the RSV port 162C to the bypass port 162D. In the illustrated position, the third channel 160C is geometrically designed and positioned to only fluidically couple the RSV port 162C and the bypass port 162D, while maintaining fluid isolation of the remaining ports 162.

As set forth above, the CLSV 68 also includes an air inlet port 162E, which allows the aspiration of air into the fluidic system 120 and may be useful for diagnostic or other purposes. The orientation illustrated in FIG. 8E (e.g., produced by counterclockwise rotation of the movable portion 152 from FIG. 8D), for instance, referred to hereafter as the "Air to Lane Groups A & B" position, fluidically couples the air inlet port 162E to both lane group A port 162A and lane group B port 162B using a fourth channel 160D. The illustrated orientation may be useful to dry the lane groups A and B prior to pressure testing or other protocols.

The orientation illustrated in FIG. 8F, referred to hereafter as the "Air to Bypass" position, may be produced by further rotation of the movable portion 152. In this configuration, the first channel 160A fluidically couples the air inlet port 162E to the bypass port 162D, which is useful to enable air to be introduced into the fluidic system 120 during certain pressure tests. It should be noted that the second channel 160B may also produce this fluidic coupling.

The orientations of the CLSV 68 illustrated in FIGS. 8A-8F, as well as other potential positions, may also be useful for diagnostic purposes to enable the processor 100 to isolate, prepare, and test the various flow paths of the fluidic system. Example flow paths of fluid through the fluidic system 120 resulting from certain of the positions of the CLSV 68 described above (specifically, those involving the RSV 66) are depicted in FIGS. 9A-9D.

Figure 9A:
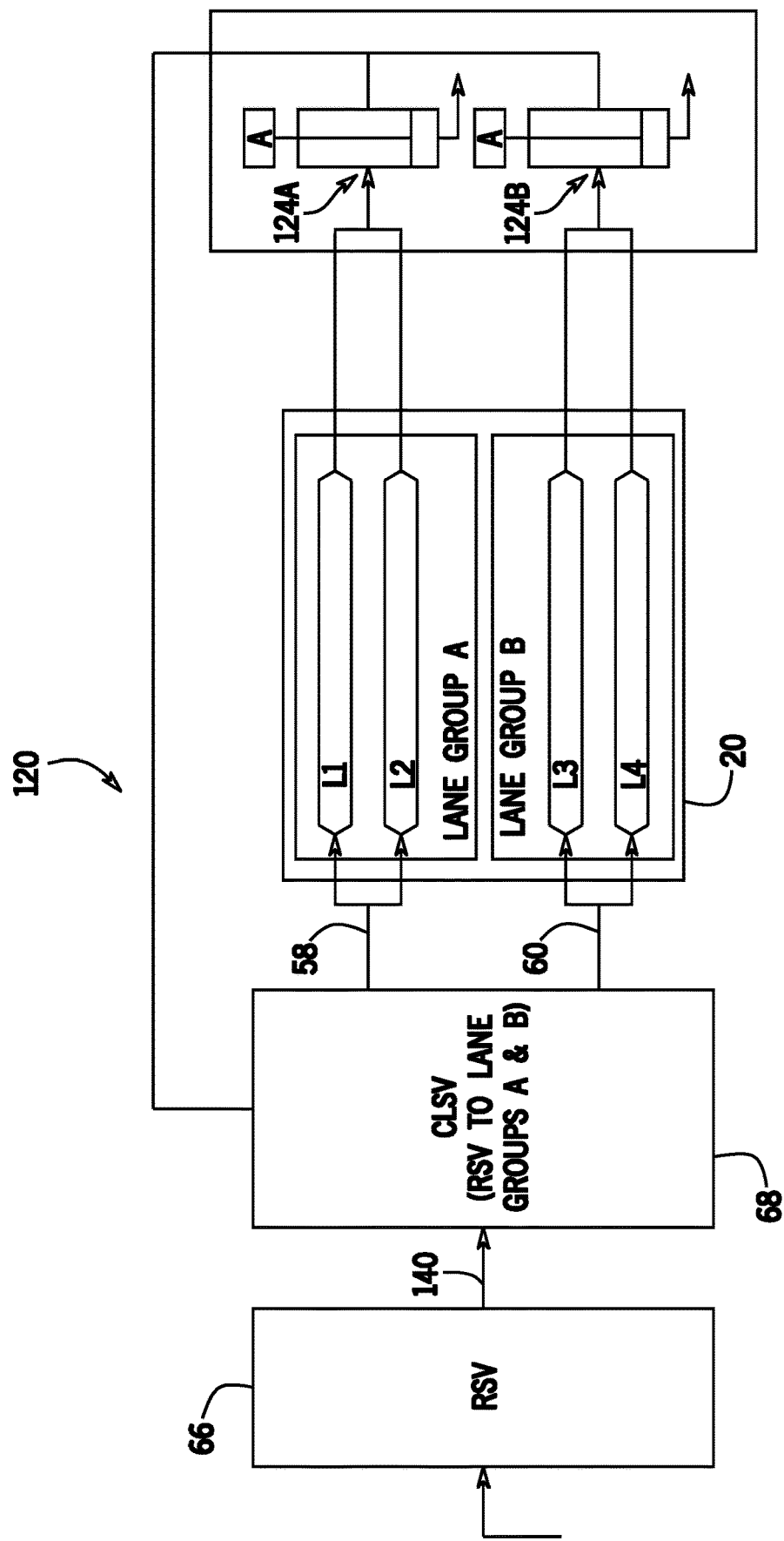
FIGS. 9A through 9D are diagrammatical overviews of various flow paths through a flow cell of the sequencing system of FIG. 1, the various flow paths being selected by the common line selector valve.

In the implementation depicted in FIG. 9A, the CLSV 68 is in the "RSV to Lane Groups A&B" position described with respect to FIG. 8A. Accordingly, during operation, the RSV 66 selects a reagent 64, which is advanced through the RSV to CLSV common line 140 to the CLSV 68. Because the RSV port 162C is fluidically coupled to the lane group A and B ports 162A and 162B via the CLSV 68, the reagent flows through the CLSV 68 and to the lane groups A and B via common lines 58 and 60, respectively. In the implementation of FIG. 9A, this is shown as both lane groups A and B being shaded, along with bold arrows indicating flow advancement though the flow cell 20 and to the syringe pumps 124. This configuration may be considered to represent the highest level of sequencing throughput for the flow cell 20.

Figure 9B:
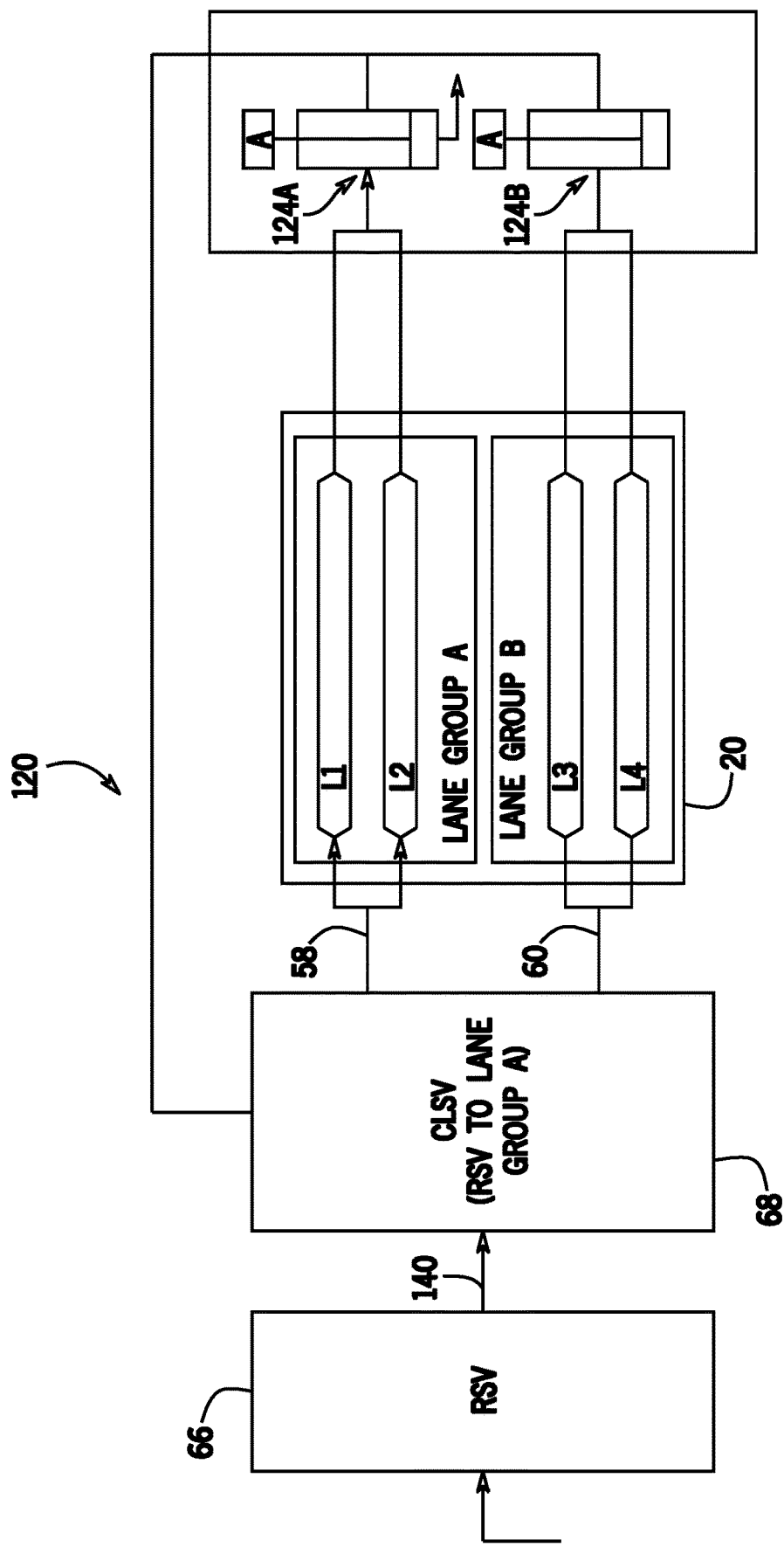

In the implementation depicted in FIG. 9B, the CLSV 68 is in the "RSV to Lane Group A" position described with respect to FIG. 8B. Accordingly, during operation, the RSV 66 selects a reagent 64, which is advanced through the common line 140 to the CLSV 68. Because the RSV port 162C is fluidically coupled only to the lane group A port 162A via the CLSV 68, the reagent flows through the CLSV 68 and to lane group A (lanes 1 and 2, L1 and L2) via common line 58. In the implementation of FIG. 9B, this is shown as only lane group A being shaded, along with bold arrows on line 58 indicating flow advancement though the flow cell 20 and to the corresponding syringe pump 124A. This allows sequencing operations in lane group A that are separate and distinct from the sequencing operations carried out in lane group B, and allows parameters of the sequencing operations to be independently controlled between the lane groups A and B.

Figure 9C:
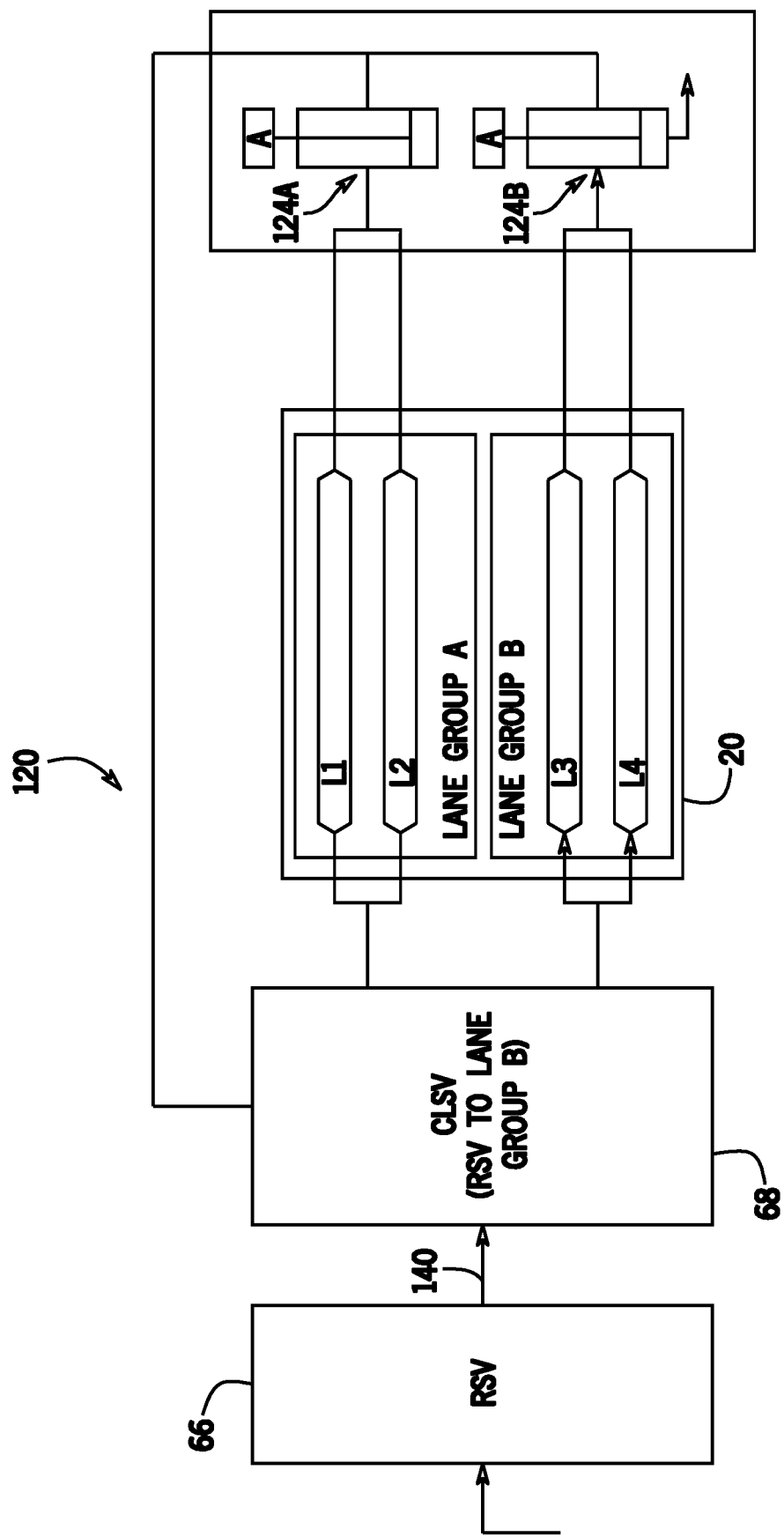

In the implementation depicted in FIG. 9C, the CLSV 68 is in the "RSV to Lane Group B" position described with respect to FIG. 8C. Accordingly, during operation and at the command of the control circuitry, the RSV 66 selects a reagent 64, which is advanced through the common line 140 to the CLSV 68. Because the RSV port 162C is fluidically coupled only to the lane group B port 162B via the CLSV 68, the reagent flows through the CLSV 68 and to lane group B (lanes 3 and 4, L3 and L4) via common line 58. In the implementation of FIG. 9B, this is shown as only lane group B being shaded, along with bold arrows on line 58 indicating flow advancement though the flow cell 20 and to the corresponding syringe pump 124B.

As set forth above, in certain implementations it may be desirable to isolate the lane groups from the output of the CLSV 68, while also allowing certain reagents to flow through the CLSV 68, for example to prime the fluidics system 120 for the introduction of new reagents during a sequence. For example, during certain protocols, it may be desirable to fill the fluidics extending from the RSV 66 and through the CLSV 68 with a reagent to be used. In such implementations, the CLSV 68 may be positioned in the "RSV to Bypass" position described with respect to FIG. 8D. In the illustrated implementation, the CLSV 68 is positioned such that the RSV port 162C is fluidically coupled only to the bypass port 162D, thereby allowing fluid to flow between the bypass line 142 and the CLSV 68, but not between the CLSV 68 and the lane groups A and/or B. This is illustrated as bold arrows leading from the CLSV 68, through the bypass line 142, and to syringe pump 124A. It should be noted that either or both syringe pumps 124A and 124B may be used in combination with the bypass line 142, but in one particular implementation, the bypass line 142 is used in conjunction only with syringe pump 124A.

Figure 10:
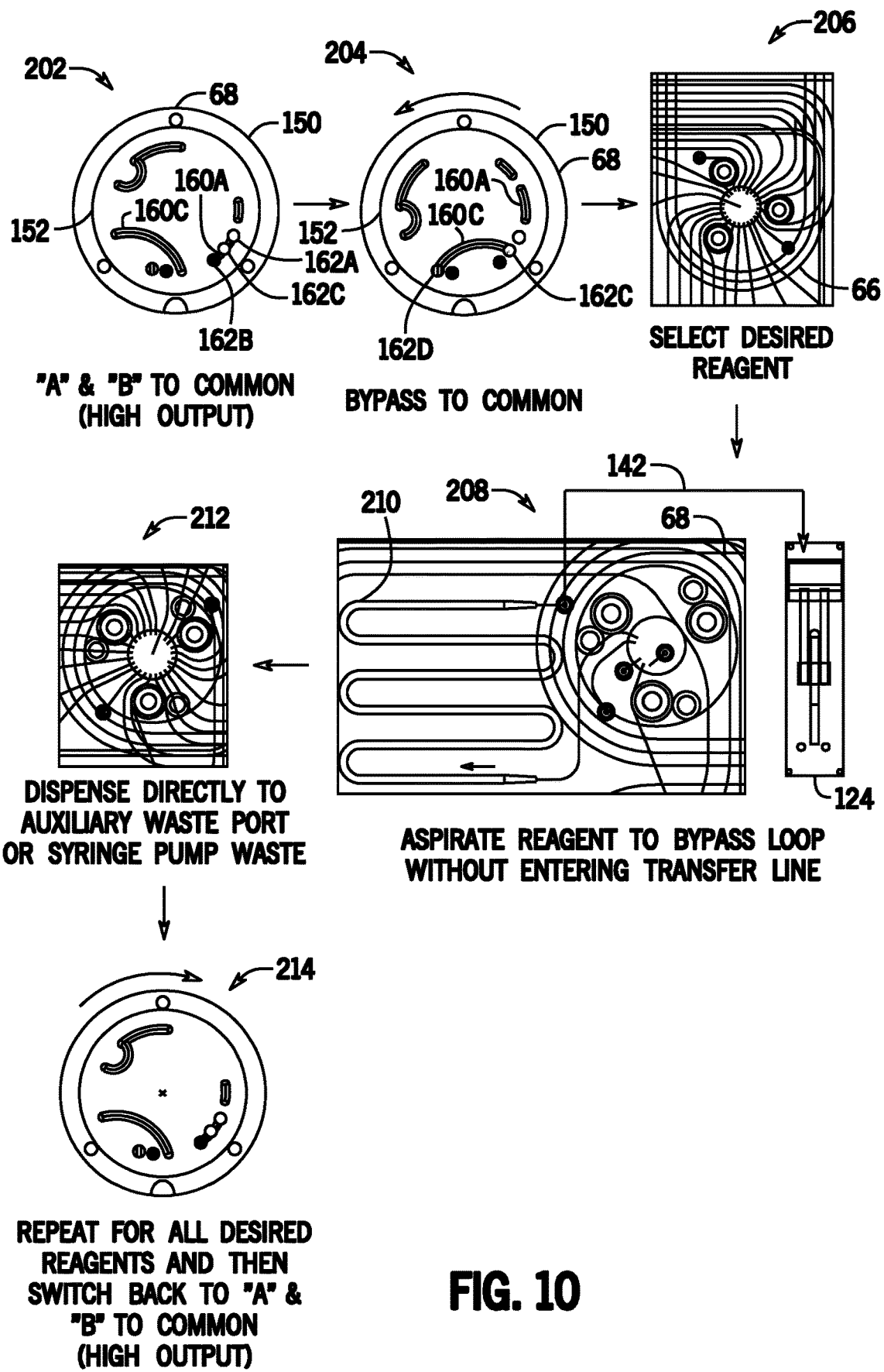
FIG. 10 is an illustration of an example method of priming the fluidic system without aspirating fluid into a flow cell of the sequencing system of FIG. 1.

An example sequence of operations using the bypass port 162D is depicted in FIG. 10, which is a method 200 of priming certain parts of the fluidic system 120 without aspirating fluid through the flow cell 20. It should be noted that such priming is often important in sequencing operations, which utilize fluid amounts on the order of microliters. Accordingly, any materials still present within the fluidic lines may cause inaccuracies in measurements, may cause variations in relative reagent amounts, and so forth.

To begin the priming sequence and as first shown at 202, the CLSV 68 is in a first position, in this case in the "high output" position, which is denoted above as the "RSV to Lane Groups A&B" position. In this position, the fluidic system 120 may have completed a protocol to prepare the flow cell 20 for introduction of one or more of the reagents 64.

Figure 9D:
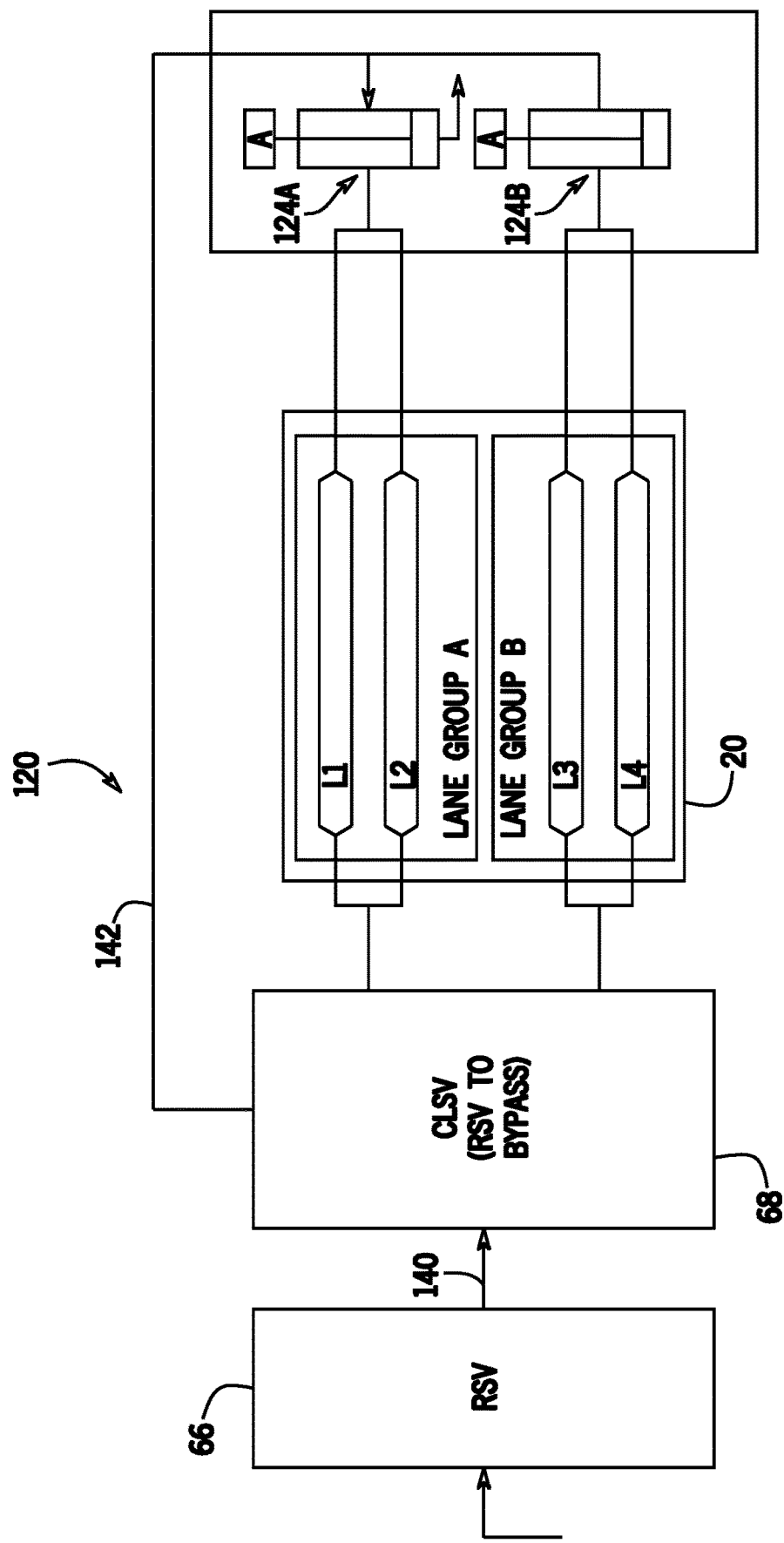

To prepare the fluidic system 120 to receive and use new reagents, the CLSV 68 may be moved (e.g., by a motor and associated controller) to a second position, shown at 204 as the "RSV to Bypass" position discussed with respect to FIG. 9D. Again, in this position, the bypass port 162D and the RSV port 162C are fluidically connected. As shown in transitioning from 202 to 204, the CLSV 68 may be displaced from the first position to the second position by counterclockwise movement of the movable portion 152 relative to the stationary portion 150. This causes the third channel 160C to be moved to the position to fluidically couple the RSV port 162C and the bypass port 162D.

The RSV 66 is also controllably positioned (e.g., by a motor and associated controller) to select the desired reagent, as shown at 206. The RSV 66 may have a number of different positions corresponding to various available reagents, and, when appropriately selected, may be subsequently aspirated through the RSV 66 and into the common line 140 toward the CLSV 68. Such aspiration, as shown at 208, may be accomplished using one or more of the syringe pumps 124. In the illustrated implementation, the syringe pump 124 is fluidically connected to the bypass line 142, which is in turn fluidically coupled to a bypass loop 210, which may serve as a cache for substances to be used for priming and/or flushing the fluidic system 120. The bypass loop 210 may have a diameter or width that is greater than a diameter or width of the common lines 58, 60, for example to enable caching of appropriate amounts of buffer, reagents, and so forth. In accordance with the illustrated implementation, the selected reagent 64 is aspirated into the bypass loop 210 without entering the bypass line 142.

Once the reagent is appropriately aspirated into the bypass loop 210, the reagent may be dispensed directly into an auxiliary waste port of the RSV 66 or into a syringe pump waste. For example, as shown at 212, this may be performed by transitioning the RSV 66 to its waste port, and causing the syringe pump 124 to pressurize the bypass line 142 and bypass loop 210 to motivate the reagent in a backward flow direction compared to the aspiration performed at 208. As shown at 214, the processes previously noted may be performed for each reagent for which priming is desired, followed by a transition of the CLSV 68 back to an appropriate sequencing position (e.g., the RSV to Lane Groups A&B position).

Figure 11:
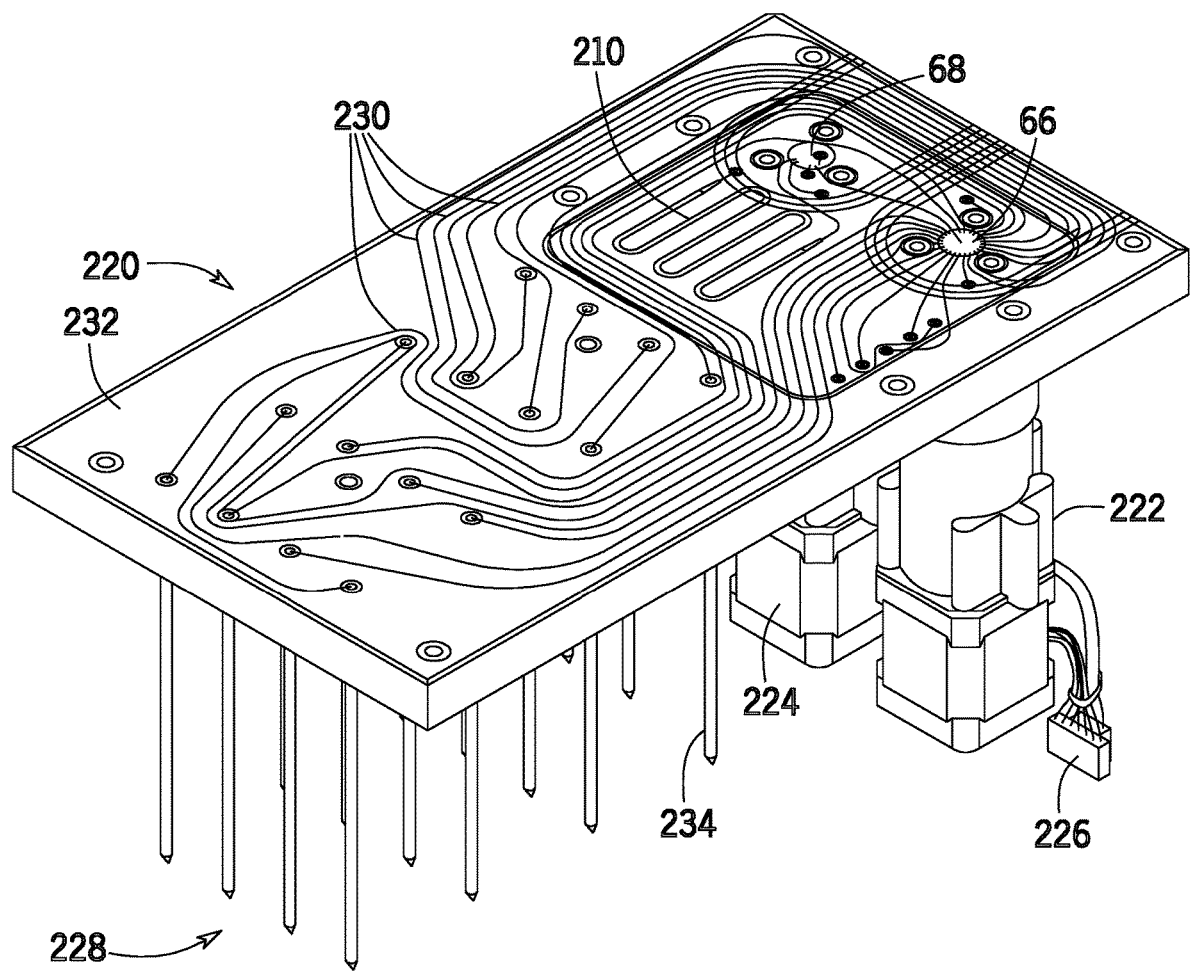
FIG. 11 is a perspective view of an implementation of a manifold assembly having a reagent selector valve, a common line selector valve, nozzles, and various fluidic channels for interfacing with the sequencing system of FIG. 1.

The nature of various connections, fluidic lines, and so forth, of the various features described herein may be further appreciated with reference to FIG. 11, which is a perspective view of a manifold assembly 220 having the RSV 66, the CLSV 68, the bypass loop 210, and various fluidic connections. The manifold assembly 220, in certain implementations, may be considered a sipper manifold assembly that is configured to interface with various reagent containers to allow the RSV 66 to select such reagents from their sources for eventual delivery to the flow cell 20.

The manifold assembly 220 includes channels formed to define flow paths for the reagents and other fluids. As can be seen in FIG. 11, the valves 66 and 68 are driven and controlled by motors 222 and 224. One or more motor interfaces or connections 226 provide power and, where desired, signals to and from the motors. As noted above, the motors (and thereby the valves) are controlled by the control circuitry during testing, commissioning, and servicing, as well as during sequencing operations.

The reagent and fluid pathways within the manifold assembly 220 are coupled to sippers 228 that, during operation, draw reagents and other fluids from respective recipients (not shown). The flow paths for the reagents and fluids, designated generally by reference 230 in FIG. 11, may be formed in a body 232 (e.g., a monolithic structure) of the manifold assembly 220 by molding, etching, or any other suitable process to allow the reagents and fluids to move from the sippers to the valves when the pump discussed above is commanded to aspirate the reagents and fluids. At least one of the sippers is configured as a nozzle sipper 234 to assist in mixing of reagents during the sequencing operation (e.g., prior to reactions and imaging). Also illustrated in FIG. 11 is the bypass loop 210 in which reagents and fluids can be drawn and moved for mixing (e.g., thereby serving as a mixing volume) and priming of the fluidic system 120 as appropriate. In implementations in which the bypass loop or bypass line serves as the mixing volume, the mixing volume may be a portion or all of the bypass line 62 or the bypass loop 210. For example, reagents may be aspirated into the bypass loop or line in a desired sequence but such that the reagents do not traverse the entire length of the bypass loop or line (which may cause them to be routed to disposal). Once the bypass line (or a portion thereof serving as the mixing volume) has been loaded with the desired sequence of reagents, the end of the bypass line through which the reagents were introduced may be switched, using a valve, so as to fluidically connect with a flow path leading to, for example, a destination recipient so that the entire set of reagents loaded into the bypass line may then be expelled back out of the bypass line and into the destination recipient. The destination recipient, for example, may be a container, tube, or other vessel designed to contain the reagents. The destination recipient may, for example, be used as a temporary work volume to which reagents and/or other materials may be transferred in order to prepare them for delivery, e.g., by mixing, to the flow cell. Thus, reagents and other fluids may, once prepared in the destination recipient, be transferred from the destination recipient to the flow cells.

It is to be understood that the phrase "fluidically connected" or the like may be used herein to describe connections between two or more components that place such components in fluidic communication with one another, much in the same manner that "electrically connected" may be used to describe an electrical connection between two or more components. The phrase "fluidically interposed" may be used, for example, to describe a particular ordering of components. For example, if component B is fluidically interposed between components A and C, then fluid flowing from component A to component C would flow through component B before reaching component C.

Figure 12:
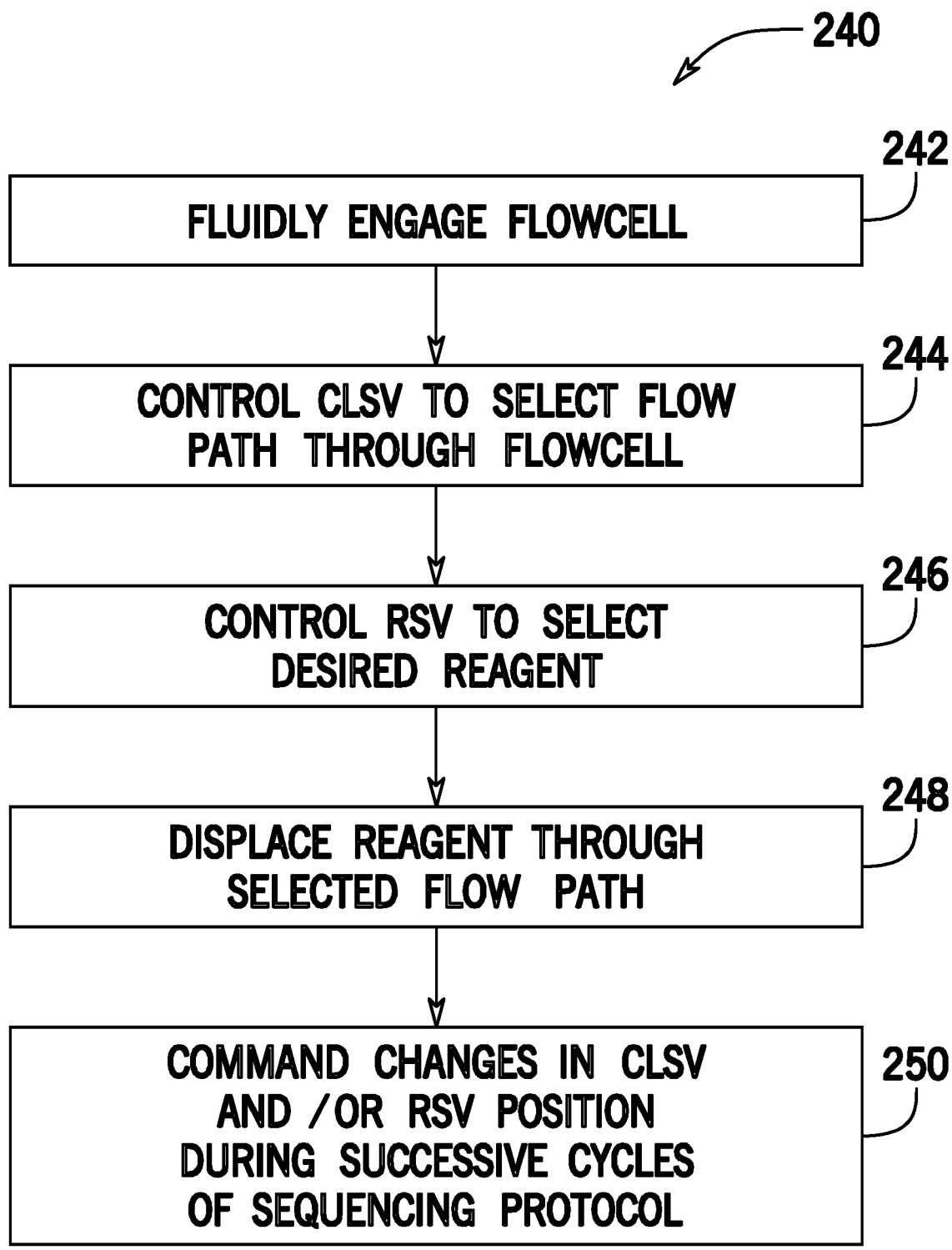
FIG. 12 is a flow diagram of an implementation of a method of operating the sequencing system of FIG. 1.

Various methods of operating the sequencing system may be performed in accordance with the implementations described herein. As one example, FIG. 12 depicts an implementation of a method 240 of operating a sequencing system having the CLSV 68, for example to individually address lane groups of the flow cell 20. All or a portion of the method 240 may be performed based on instructions executed by the control circuitry, for example during a sequencing protocol, testing protocol, or the like. Further, it should be noted that certain of the actions described herein may be performed in a different order than those presented, or altogether omitted, and that other operations may be included in the method 240 as appropriate.

As noted above, certain components of the sequencing system may be removable, replaceable, or disposable. In certain implementations, for example, the flow cell 20 may be a part of a disposable cartridge or similar structure having features configured to interface with various connectors of the sequencing system. Accordingly, the method 240 includes fluidically engaging (block 242) the flow cell 20 with one or more (e.g., a plurality of) manifolds between the CLSV 68 and the flow cell 20, for example when the control circuitry determines that the flow cell 20 has been mounted into the sequencing system. The fluid engagement results in engagement of the flow cell 20 with the CLSV 68, which occurs prior to displacing reagents from the RSV 66 and CLSV 68.

The method 240 also includes controlling (block 244) the CLSV 68 (e.g., its position) to select a flow path through the flow cell 20 from a plurality of flow paths through the flow cell. For example, selecting a flow path through the flow cell 20 may include selecting which lanes fluid will flow through within the flow cell 20. Referring to FIGS. 9A through 9C, for example, the control circuitry may select between a first flow path flowing only through the lane group A (e.g., as shown in FIG. 9B), a second flow path flowing only through the lane group B (e.g., as shown in FIG. 9C), or a third flow path that includes both the first and second flow paths (e.g., as shown in FIG. 9A).

Selection of appropriate flow paths for the reagent may be performed in concert with the selection of appropriate reagents for the flow cell 20. Thus, the method 240 may include controlling (block 246) the RSV 66, which is fluidically upstream of the CLSV 68, to select different reagents from a plurality of reagents for displacement through the CLSV 68 and the flow cell 20 in accordance with the sequencing protocol.

The method 240 then includes displacing (block 248) a reagent through the selected flow path in accordance with the sequencing protocol. For example, the control circuitry may cause the pump 38 to draw the selected reagent through the RSV 66, through the RSV to CLSV common line 140, through the CLSV 66, and through the selected flow path through the flow cell 20.

During various sequencing operations various reagents may be utilized, meaning that various positions of the CLSV 68 and/or RSV 66 may be selected to appropriately transition between the reagents. Accordingly, the method 240 includes commanding (block 250) changes in positions of the CLSV 68 and/or the RSV 66 during successive cycles of the sequencing protocol. The successive cycles may be cycles of reagent introduction into the flow cell 20, or an entire cycle of a sequencing reaction sequence, or both. For instance, changes in the position of the RSV 66 and the CLSV 68 may be performed as described with respect to FIG. 10 to transition between reagents. Indeed, such transitioning may involve commanding the CLSV 68 to select a bypass line rather than a flow path through the flow cell 20, for example to carry out reagent priming of certain fluidic structures of the manifold assembly 220.

Figure 13:
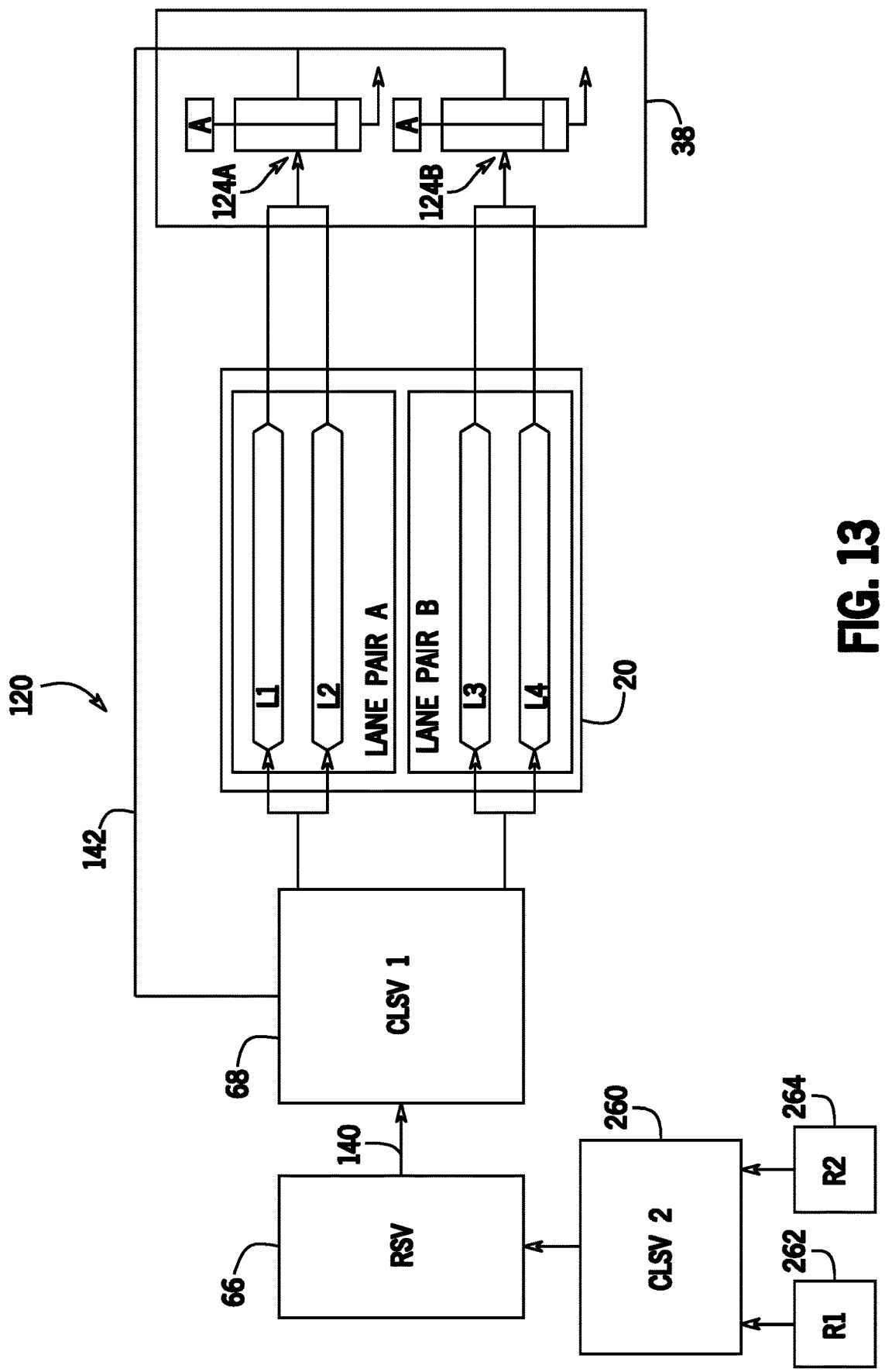
FIG. 13 is a schematic overview of another implementation of the fluidic system for the sequencing system of FIG. 1 and having an additional common line selector valve to select between and combine various reagents.

It should be appreciated that the CLSV 68 described herein may additionally or alternatively be employed to select between and/or combine different common lines. For example, in one implementation and as schematically shown in FIG. 13, an additional CLSV 260 may be positioned upstream of the CLSV 68 positioned between the RSV 66 and the flow cell 20. The additional CLSV 260 may be utilized to select between, for example, ports leading to various reagents to enable the reagents to be drawn into the additional CLSV 260 and subsequent fluidics in various combinations. As one example, the additional CLSV 260 may be commanded by the control circuitry to transition to a position to fluidically couple ports leading to a first reagent source 262 and a second reagent source 264. By fluidically coupling the ports together in this way, the additional CLSV 260 allows the first and second reagents to be aspirated into the fluidic system 120 simultaneously, for example by action of the pump 38. A port of the RSV 66 corresponding to the combination from the additional CLSV 260 may be selected to allow fluid coupling to the CLSV 68 and, subsequently, the flow cell 20.

As one example, such a configuration may be particularly useful to avoid packaging and shipping large volumes of substances that can otherwise be diluted with a liquid that can be locally sourced. In the context of a buffer, for example, the first reagent source 262 may be a concentrated buffer solution, and the second reagent source 264 may be a diluent, such as water. In certain situations, it may be useful to fluidically couple the first and second reagent sources 262, 264 as shown such that the concentrated buffer solution becomes diluted to an appropriate extent. It is presently contemplated that the use of additional valving may be appropriate to further control the relative mixing amounts of different reagents (e.g., to control relative flow rates).

The use, if any, of ordinal indicators, e.g., (a), (b), (c) . . . or the like, in this disclosure and claims is to be understood as not conveying any particular order or sequence, except to the extent that such an order or sequence is explicitly indicated. For example, if there are three steps labeled (i), (ii), and (iii), it is to be understood that these steps may be performed in any order (or even concurrently, if not otherwise contraindicated) unless indicated otherwise. For example, if step (ii) involves the handling of an element that is created in step (i), then step (ii) may be viewed as happening at some point after step (i). Similarly, if step (i) involves the handling of an element that is created in step (ii), the reverse is to be understood.

It is also to be understood that the use of "to," e.g., "a valve to switch between two flow paths," may be replaceable with language such as "configured to," e.g., "a valve configured to switch between two flow paths", or the like.

Terms such as "about," "approximately," "substantially," "nominal," or the like, when used in reference to quantities or similar quantifiable properties, are to be understood to be inclusive of values within ±10% of the values specified, unless otherwise indicated.

In addition to the claims listed in this disclosure, the following additional implementations are to be understood to be within the scope of this disclosure:

Implementation 1: A system including: a flowcell to support analytes of interest; a selector valve coupled to the flowcell to select a flow path through the flowcell from a plurality of flow paths; a pump coupled to the flowcell to displace fluids through the selected flow path during an analysis operation; and control circuitry coupled to the selector valve to command the selector valve to select the selected flow path.

Implementation 2: The system of implementation 1, in which the plurality of flow paths includes a first flow path through one channel of the flowcell, and a second flow path through a second channel of the flowcell different from the first flow path.

Implementation 3: The system of implementation 2, in which the plurality of flow paths includes a third flow path that includes both the first and the second flow paths.

Implementation 4: The system of implementation 1, in which the selector valve is coupled to a bypass line that bypasses the flowcell, and in which the selector valve also controllable to select the bypass line rather than a flow path through the flowcell.

Implementation 5: The system of implementation 1, in which, during the analysis operation the control circuitry automatically commands the selector valve to select the selected flow path based upon an analysis protocol.

Implementation 6: The system of implementation 1, including a reagent selector valve fluidly upstream of the selector valve to select a reagent from a plurality of reagents and to direct the selected reagent to an inlet of the selector valve.

Implementation 7: The system of implementation 1, including a plurality of manifolds coupled fluidly between the selector valve and the flowcell to engage the flowcell with the selector valve when the flowcell is mounted in a sequencing system.

Implementation 8: The system of implementation 1, in which the pump includes a syringe pump fluidly downstream of the flowcell.

Implementation 9: A system including: a reagent selector valve to select a reagent from a plurality of reagents in accordance with an analysis protocol; a flowcell to support analytes of interest; a selector valve coupled between the reagent selector valve and the flowcell to select a flow path through the flowcell from a plurality of flow paths and to direct the selected reagent through the selected flow path in accordance with the analysis protocol; a pump coupled to the flowcell to displace the selected reagent through the selected flow path in accordance with the analysis protocol; and control circuitry coupled to the selector valve to command the selector valve to select the selected flow path.

Implementation 10: The system of implementation 9, in which the plurality of flow paths includes a first flow path through one channel of the flowcell, and a second flow path through a second channel of the flowcell different from the first flow path.

Implementation 11: The system of implementation 10, in which the plurality of flow paths includes a third flow path that includes both the first and the second flow paths.

Implementation 12: The system of implementation 9, in which the selector valve is coupled to a bypass line that bypasses the flowcell, and in which the selector valve also controllable to select the bypass line rather than a flow path through the flowcell.

Implementation 13: The system of implementation 9, including a plurality of manifolds coupled fluidly between the selector valve and the flowcell to engage the flowcell with the selector valve when the flowcell is mounted in a sequencing system.

Implementation 14: A method including: controlling a selector valve fluidly upstream of a flowcell to select a flow path through the flowcell from a plurality of flow paths through the flowcell; displacing a reagent through the selected flow path in accordance with an analysis protocol; in which the plurality of flow paths includes a first flow path through one channel of the flowcell, a second flow path through a second channel of the flowcell different from the first flow path, and a third flow path that includes both the first and the second flow paths.

Implementation 15: The method of implementation 14, including controlling a reagent selector valve fluidly upstream of the selector valve to select different reagents from a plurality of reagents for displacement through the selector valve and the flowcell in accordance with the analysis protocol.

Implementation 16: The method of implementation 15, including commanding changes in positions of the selector valve and/or the reagent selector valve during successive cycles of the analysis protocol.

Implementation 17: The method of implementation 14, including commanding the selector valve to select a bypass line rather than a flow path through the flowcell.

Implementation 18: The method of implementation 14, including fluidly engaging the flowcell with a plurality of manifolds between the selector valve and the flowcell to engage the flowcell with the selector valve when the flowcell is mounted in a sequencing system and prior to displacing the reagent.

Implementation 19: The method of implementation 14, in which the reagent is displaced through the selected flow path by a pump fluidly downstream of the flowcell.

Implementation 20: The method of implementation 19, in which the pump includes a syringe pump.

It should be appreciated that all combinations of the foregoing concepts (provided such concepts are not mutually inconsistent) are contemplated as being part of the inventive subject matter disclosed herein. All combinations of the claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

What is claimed is:

1. A system comprising:
   a plurality of flow paths to fluidically connect with a flow cell to support analytes of interest when the flow cell is mounted in the system;
   a flow path selector valve coupled to the flow paths, the flow path selector valve to select between the flow paths;
   a pump to fluidically connect with the flow cell when the flow cell is mounted in the system and to displace fluids through one of the flow paths selected by the flow path selector valve during an analysis operation; and
   control circuitry operatively coupled to the flow path selector valve, the control circuitry having one or more processors and a memory to store computer-executable instructions which, when executed by the one or more processors, control the one or more processors to command the flow path selector valve to select the selected flow path, wherein the plurality of flow paths comprise a first flow path coupled to a first channel of the flow cell and a second flow path coupled to a second channel of the flow cell and wherein the flow path selector valve is adjustable between a first state in which the flow path selector valve selects the first flow path, a second state in which the flow path selector valve selects the second flow path, and a third state in which the flow path selector valve selects both the first flow path and the second flow path.

2. The system of claim 1, wherein the flow path selector valve is further fluidically coupled to a bypass line that bypasses the flow cell when the flow cell is mounted in the system, and wherein the flow path selector valve is further adjustable into a fourth state in which the flow path selector valve selects the bypass line rather than the flow paths.

3. The system of claim 1, wherein, during the analysis operation the control circuitry automatically commands the flow path selector valve to select the selected flow path based upon an analysis protocol.

4. The system of claim 1, further comprising a reagent selector valve positioned fluidically upstream of the flow path selector valve and to select a reagent from a plurality of reagents and to direct the selected reagent to an inlet of the flow path selector valve.

5. The system of claim 1, comprising one or more manifolds to fluidically connect the flow cell with the flow path selector valve when the flow cell is mounted in the system, wherein the one or more manifolds are fluidically interposed between the flow path selector valve and the flow cell when the flow cell is mounted in the system.

6. The system of claim 1, wherein the pump comprises a syringe pump located fluidically downstream of the flow cell.

7. A system comprising:
   a reagent selector valve to select a reagent from a plurality of reagents in accordance with an analysis protocol;
   a flow cell to support analytes of interest;
   a flow path selector valve fluidically interposed between the reagent selector valve and the flow cell, the flow path selector valve to select a flow path through the flow cell from a plurality of flow paths through the flow cell, and to direct the selected reagent through the selected flow path in accordance with the analysis protocol;
   a pump that is fluidically connected with the flow cell, the pump to displace the selected reagent through the selected flow path in accordance with the analysis protocol; and
   control circuitry operatively coupled to the flow path selector valve, the control circuitry having one or more processors and a memory to store computer-executable instructions which, when executed by the one or more processors, control the one or more processors to cause the flow path selector valve to select the selected flow path, wherein:
      the plurality of flow paths comprise a first flow path through one channel of the flow cell and a second flow path through a second channel of the flow cell,
      the flow path selector valve comprises at least one moveable portion, and
      the at least one moveable portion is moveable into a first position that selects the first flow path but not the second flow path, a second position that selects the second flow path but not the first flow path, and a third position that selects both the first and second flow paths.

8. The system of claim 7, wherein the flow path selector valve is further fluidically connected with a bypass line that bypasses the flow cell, and wherein the at least one moveable portion is further moveable into a fourth position that selects the bypass line rather than a flow path through the flow cell.

9. The system of claim 7, comprising one or more manifolds fluidically coupled between the selector valve and the flow cell to engage the flow cell with the selector valve when the flow cell is mounted in a sequencing system.

10. A method comprising:
    controlling, using control circuitry, a flow path selector valve fluidly upstream of a flow cell to select one or more flow paths through the flow cell from a plurality of flow paths through the flow cell; and
    pumping, using a pump, a reagent through the one or more selected flow paths in accordance with an analysis protocol, wherein the plurality of flow paths comprises a first flow path through one channel of the flow cell and a second flow path through a second channel of the flow cell, wherein the second flow path is different from the first flow path, and wherein the flow path selector valve is adjustable between a first state in which the flow path selector valve selects the first flow path, a second state in which the flow path selector valve selects the second flow path, and a third state in which the flow path selector valve selects both the first flow path and the second flow path.

11. The method of claim 10, further comprising controlling a reagent selector valve fluidically connected with the flow path selector valve, the reagent selector valve to select different reagents from a plurality of reagents for displacement through the flow path selector valve and the flow cell in accordance with the analysis protocol, wherein the flow path selector valve is fluidically interposed between the reagent selector valve and the flow cell.

12. The method of claim 11, further comprising commanding changes in positions of the flow path selector valve, the reagent selector valve, or the flow path selector valve and the reagent selector valve during successive cycles of the analysis protocol.

13. The method of claim 10, further comprising commanding the flow path selector valve to select a bypass line that bypasses the flow cell rather than a flow path through the flow cell.

14. The method of claim 10, further comprising mounting the flow cell in a sequencing system to fluidically connect the flow cell with a plurality of manifolds fluidically interposed between the flow path selector valve and the flow cell to fluidically connect the flow cell with the flow path selector valve, wherein the mounting of the flow cell is performed prior to displacing the reagent.

15. The method of claim 10, wherein the pump is positioned downstream of the flow cell.

16. The method of claim 15, wherein the pump comprises a syringe pump.

17. The method of claim 10 further comprising:
commanding the flow path selector valve into the third state such that the flow path selector valve selects both the first flow path and the second flow path; and
pumping, using the pump, the reagent through both the first flow path and the second flow path by simultaneously:
  pumping, using the pump, a first portion of the reagent through the first flow path and the first channel of the flow cell; and
  pumping, using the pump, a second portion of the reagent through the second flow path and the second channel of the flow cell.

18. A method comprising:
controlling a flow path selector valve fluidly upstream of a flow cell to select a flow path through the flow cell from a plurality of flow paths through the flow cell;
displacing a reagent through the selected flow path in accordance with an analysis protocol, wherein the plurality of flow paths comprises a first flow path through one channel of the flow cell, a second flow path through a second channel of the flow cell, and a third flow path that includes both the first and the second flow paths, wherein the second flow path is different from the first flow path;
controlling the flow path selector valve to select the third flow path; and
displacing the reagent through the third flow path by simultaneously:
  displacing a first portion of the reagent through the first flow path and the first channel of the flow cell; and
  displacing a second portion of the reagent through the second flow path and the second channel of the flow cell.

* * * * *